(12) United States Patent
Kadereit et al.

(10) Patent No.: US 9,321,787 B2
(45) Date of Patent: Apr. 26, 2016

(54) CARBOXYLIC ACID DERIVATIVES HAVING AN OXAZOLO[5,4-D]PYRIMIDINE RING

(75) Inventors: Dieter Kadereit, Frankfurt am Main (DE); Matthias Schaefer, Frankfurt am Main (DE); Stephanie Hachtel, Frankfurt am Main (DE); Thomas Huebschle, Frankfurt am Main (DE); Katrin Hiss, Frankfurt am Main (DE)

(73) Assignee: SANOFI, Paris (FR)

( * ) Notice: Subject to any disclaimer, the term of this patent is extended or adjusted under 35 U.S.C. 154(b) by 821 days.

(21) Appl. No.: 13/532,292

(22) Filed: Jun. 25, 2012

(65) Prior Publication Data

US 2013/0023544 A1     Jan. 24, 2013

(30) Foreign Application Priority Data

Jul. 7, 2011    (EP) ..................................... 11305878
May 11, 2012    (EP) ..................................... 12305526

(51) Int. Cl.
     *C07D 498/04*           (2006.01)

(52) U.S. Cl.
     CPC ................................... *C07D 498/04* (2013.01)

(58) Field of Classification Search
None
See application file for complete search history.

(56) References Cited

U.S. PATENT DOCUMENTS

| | | | |
|---|---|---|---|
| 7,186,413 B2 * | 3/2007 | Bouhadir et al. | ............. 424/400 |
| 8,580,816 B2 | 11/2013 | Kadereit et al. | |
| 8,735,402 B2 | 5/2014 | Kadereit et al. | |
| 8,748,436 B2 | 6/2014 | Kadereit et al. | |
| 8,785,439 B2 | 7/2014 | Kadereit et al. | |
| 8,846,690 B2 | 9/2014 | Kadereit et al. | |
| 8,846,691 B2 | 9/2014 | Kadereit et al. | |
| 8,846,692 B2 * | 9/2014 | Kadereit et al. | ........... 514/260.1 |
| 8,907,093 B2 | 12/2014 | Kadereit et al. | |
| 9,040,544 B2 | 5/2015 | Kadereit et al. | |
| 2013/0023544 A1 | 1/2013 | Kadereit et al. | |

FOREIGN PATENT DOCUMENTS

| | | | |
|---|---|---|---|
| WO | WO 01/15750 A1 * | 3/2001 |
| WO | WO2009/154775 A1 | 12/2009 |
| WO | WO2010/006704 A1 | 1/2010 |
| WO | WO 2011/086079 A1 * | 7/2011 |

OTHER PUBLICATIONS

International Report dated Aug. 3, 2012 issued in PCT/EP2012/063298.
European Search Report dated Oct. 19, 2011 issued in EP11305878.
CAS Registry No. 1417620-21-3 (2013). "Preparation of Substituted Oxazolopyrimidine Derivatives as EDG-1 Receptor Activators," one page.

* cited by examiner

*Primary Examiner* — Leslie A. Royds Draper
(74) *Attorney, Agent, or Firm* — Morrison & Foerster LLP

(57) ABSTRACT

The invention therefore relates to compounds of the formula I

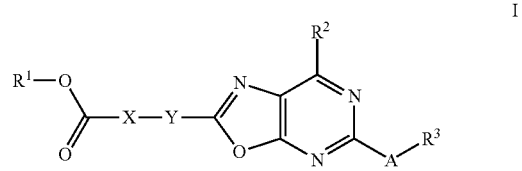

in which A, X, Y, $R^1$, $R^2$ and $R^3$ have the given meanings. The compounds of the formula I are suitable, for example, for wound healing.

7 Claims, No Drawings

CARBOXYLIC ACID DERIVATIVES HAVING AN OXAZOLO[5,4-D]PYRIMIDINE RING

The present invention relates to carboxylic acid derivatives having an oxazolo[5,4-d]pyrimidine ring, and to their physiologically acceptable salts.

Structurally similar compounds are already described in the prior art (see WO 2009/154775), which are suitable for treating multiple sclerosis. The mode of action of these compounds consists in causing a desensitization of the EDG 1 signal pathway by activating the EDG 1 receptor (so-called superagonism), which is then equivalent to a functional antagonism of the EDG 1 signal pathway. Systemically means that especially on lymphocytes, the EDG-1 signal pathway is permanently suppressed, as a result of which these cells can no longer chemotactically follow the S1P gradient between blood and lymph fluid. This means that the affected lymphocytes can no longer leave the secondary lymphatic tissue (increased homing) and the number of freely circulating lymphocytes in the plasma is greatly reduced. This deficiency of lymphocytes in the plasma (lymphopenia) brings about immunosuppression which is obligatorily required for the mechanism of action of the EDG-1 receptor modulators described in WO 2009/154775.

It was an object of the invention to provide compounds which display a therapeutically utilizable action. The object was in particular to provide novel compounds which are suitable specifically for wound healing and in particular for the treatment of wound healing disorders in patients with diabetes. In addition, it was desirable to provide compounds which are suitable for the treatment of diabetic foot syndrome (DFS). Furthermore, it was desirable to achieve a reproducible activation of the EDG 1 receptor signal pathway which thereby permits, in pharmacological terms, a persistent activation of the EDG 1 signal pathway.

The invention therefore relates to compounds of the formula I

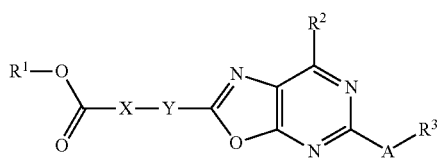

in which A, X, Y, $R^1$, $R^2$ and $R^3$ are as defined below.

The mechanism of action of the compounds of the formula I is thus not based on desensitization of the EDG 1 signal pathway and is therefore in diametral opposition to the mechanism of action described in WO 2009/154775. The invention furthermore relates to processes for the preparation of compounds of the formula I, their use, in particular as active ingredients in pharmaceuticals, and pharmaceutical compositions comprising them.

Compared with healthy people, patients with diabetes have delayed wound healing and an increased rate of infection, especially in the case of long-term hyperglycemia, caused for example by poor blood sugar regulation. The causes include circulation disorders, especially in the area of the small vessels, which lead to impaired oxygen and nutrient supply of the tissue. Moreover, the cell division and cell migration rate of keratinocytes, fibroblasts and dermal endothelial cells is reduced. Additionally, the activity of various defense cells (granulocytes) with reduced phagocytosis (engulfing and destruction of bacteria) is restricted. The action of antibodies (immunoglobulins) against bacteria at high blood sugar levels is also restricted. Accordingly, wounds and infections in patients with diabetes have to be cared for in a particular way.

The Edg-1 receptor is a member of the endothelial differentiation gene (Edg) receptor family of currently eight identified class A GPCRs (G-protein coupled receptors). This family can be divided into subfamilies of sphingosine-1-phosphate (S1P)-activated receptors (five members) and receptors activated by lysophosphatidic acid (LPA; three members). The endogenous ligand S1P is a pluripotent lysophospholipid acting on different cell types by activating GPCRs from the Edg receptor family, namely Edg-1 (=S1P1), Edg-3 (=S1P3), Edg-5 (=S1P2), Edg-6 (=S1P4) and Edg-8 (S1P5). Although S1P is also described as an intracellular messenger, numerous cellular responses of S1P are mediated via the activation of Edg receptors. S1P is generated by the enzyme family of sphingosine kinases (SPHK) and degraded by different phosphatases or lyases.

Known indications of Edg-1 receptor agonists are, for example, cardiovascular disorders, atherosclerosis, heart failure, cardioprotection, peripheral arterial occlusive disease, kidney disorders and respiratory disorders.

The present invention provides compounds of the formula I in any of their stereoisomeric forms, or a mixture of stereoisomeric forms in any ratio, or a physiologically acceptable salt thereof, or a physiologically acceptable solvate of such a compound or such a salt,

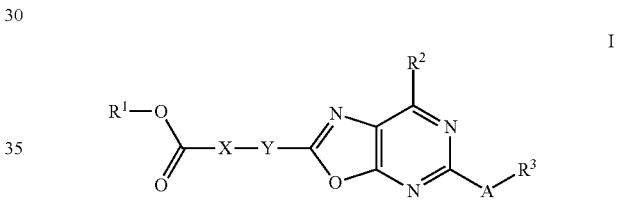

wherein
A is selected from the group consisting of a bond, —$CH_2$—, NH, O and S;
X is selected from the group consisting of ($C_1$-$C_6$)-alkanediyl, ($C_2$-$C_6$)-alkenediyl, ($C_2$-$C_6$)-alkynediyl, ($C_3$-$C_7$)-cycloalkanediyl, ($C_1$-$C_6$)-alkanediyloxy and ($C_3$-$C_7$)-cycloalkanediyloxy, all of which are optionally substituted by one or more identical or different substituents selected from the group consisting of fluorine and hydroxyl, where the oxygen atom of the ($C_1$-$C_6$)-alkanediyloxy and ($C_3$-$C_7$)-cycloalkanediyloxy groups is attached to group Y;
Y is selected from the group consisting of phenylene and a bivalent radical of an aromatic 5-membered or 6-membered monocyclic heterocycle which contains 1, 2 or 3 identical or different ring heteroatoms selected from the group consisting of N, O and S, where one of the ring nitrogen atoms may carry a hydrogen atom or a substituent $R^4$ and where the phenylene and the bivalent radical of an aromatic heterocycle are optionally substituted at one or more ring carbon atoms by identical or different substituents $R^5$;
$R^1$ is selected from the group consisting of hydrogen, ($C_1$-$C_4$)-alkyl and ($C_3$-$C_7$)-cycloalkyl-$C_zH_{2z}$—, where z is selected from the group consisting of 0, 1 and 2;
$R^2$ is selected from the group consisting of ($C_1$-$C_6$)-alkyl, ($C_3$-$C_6$)-cycloalkyl-$C_xH_{2x}$—, $Het^1$-$C_nH_{2n}$—, where x and n are selected from the group consisting of 0, 1 and 2;
$R^3$ is selected from the group consisting of ($C_1$-$C_6$)-alkyl, where the alkyl radical is optionally substituted by one or more fluorine atoms, ($C_2$-$C_6$)-alkenyl, ($C_2$-$C_6$)-alkynyl, ($C_3$-

$C_7$)-cycloalkyl-$C_uH_{2u}$— and Het²-$C_vH_{2v}$—, where u and v are selected from the group consisting of 1 and 2, or $R^3$ is a radical of a saturated or unsaturated 3-membered to 10-membered monocyclic or bicyclic ring which contains 0, 1, 2, 3 or 4 identical or different ring heteroatoms selected from the group consisting of N, O and S, where one or two of the ring nitrogen atoms may carry a hydrogen atom or a ($C_1$-$C_4$)-alkyl substituent and one or two of the ring sulfur atoms may carry one or two oxo groups and where the radical of a ring is optionally substituted at one or more ring carbon atoms by identical or different substituents $R^{31}$;

$R^4$ is selected from the group consisting of ($C_1$-$C_4$)-alkyl, ($C_3$-$C_7$)-cycloalkyl-$C_wH_{2w}$— and oxy, where w is selected from the group consisting of 0, 1 and 2;

$R^5$ is selected from the group consisting of halogen, hydroxyl, ($C_1$-$C_4$)-alkyl-, ($C_3$-$C_5$)-cycloalkyl-$C_zH_{2z}$—, ($C_1$-$C_4$)-alkyloxy, ($C_1$-$C_4$)-alkyl-S(O)$_m$—, amino, nitro, cyano, hydroxycarbonyl, ($C_1$-$C_4$)-alkyloxycarbonyl, aminocarbonyl and aminosulfonyl, where z is selected from the group consisting of 0, 1 and 2;

$R^{31}$ is selected from the group consisting of halogen, hydroxyl, ($C_1$-$C_4$)-alkyl, ($C_1$-$C_4$)-alkyloxy, ($C_3$-$C_7$)-cycloalkyl, oxo, ($C_1$-$C_4$)-alkyl-S(O)$_m$—, amino, ($C_1$-$C_4$)-alkylamino, di(($C_1$-$C_4$)-alkyl)amino, ($C_1$-$C_4$)-alkylcarbonylamino, ($C_1$-$C_4$)-alkylsulfonylamino, nitro, cyano, ($C_1$-$C_4$)-alkylcarbonyl, aminosulfonyl, ($C_1$-$C_4$)-alkylaminosulfonyl and di(($C_1$-$C_4$)-alkyl)aminosulfonyl;

Het¹ is a radical of a saturated 4-membered to 6-membered monocyclic saturated heterocycle which contains 1 or 2 identical or different ring heteroatoms selected from the group consisting of O and S and which is attached via a ring carbon atom, where a ring sulfur atom may carry one or two oxo groups and where the radical of a heterocycle is optionally substituted by one or more identical or different substituents selected from the group consisting of fluorine and ($C_1$-$C_4$)-alkyl;

Het² is a radical of a saturated 4-membered to 7-membered monocyclic heterocycle which contains 1 or 2 identical or different ring heteroatoms selected from the group consisting of N, O and S and which is attached via a ring carbon atom, where the radical of a heterocycle is optionally substituted by one or more identical or different substituents selected from the group consisting of fluorine and ($C_1$-$C_4$)-alkyl;

m is selected from the group consisting of 0, 1 and 2.

Structural elements such as groups, substituents, hetero ring members, numbers or other features, for example alkyl groups, groups like $R^5$, numbers like m, which can occur several times in the compounds of the formula I, can all independently of one another have any of the indicated meanings and can in each case be identical to or different from one another. For example, the alkyl groups in a dialkylamino group can be identical or different.

Alkyl, alkenyl and alkynyl groups can be linear, i.e. straight-chain, or branched. This also applies when they are part of other groups, for example alkyloxy groups (=alkoxy groups, alkyl O groups), alkyloxycarbonyl groups or alkyl-substituted amino groups, or when they are substituted. Depending on the respective definition, the number of carbon atoms in an alkyl group can be 1, 2, 3, 4, 5 or 6, or 1, 2, 3 or 4, or 1, 2 or 3. Examples of alkyl are methyl, ethyl, propyl including n-propyl and isopropyl, butyl including n-butyl, sec-butyl, isobutyl and tert-butyl, pentyl including n pentyl, 1-methylbutyl, isopentyl, neopentyl and tert-pentyl, and hexyl including n-hexyl, 3,3-dimethylbutyl and isohexyl. Double bonds and triple bonds in alkenyl groups and alkynyl groups can be present in any positions. In one embodiment of the invention, alkenyl groups contain one double bond and alkynyl groups contain one triple bond. In one embodiment of the invention, an alkenyl group or alkynyl group contains at least three carbon atoms and is bonded to the remainder of the molecule via a carbon atom which is not part of a double bond or triple bond. Examples of alkenyl and alkynyl are ethenyl, prop-1-enyl, prop-2-enyl (=allyl), but-2-enyl, 2-methylprop-2-enyl, 3-methylbut-2-enyl, hex-3-enyl, hex-4-enyl, prop-2-ynyl (=propargyl), but-2-ynyl, but-3-ynyl, hex-4-ynyl or hex-5-ynyl. Substituted alkyl groups, alkenyl groups and alkynyl groups can be substituted in any positions, provided that the respective compound is sufficiently stable and is suitable for the desired purpose such as use as a drug substance. The prerequisite that a specific group and a compound of the formula I are sufficiently stable and suitable for the desired purpose such as use as a drug substance, applies in general with respect to the definitions of all groups in the compounds of the formula I.

As far as applicable, the preceding explanations regarding alkyl, alkenyl and alkynyl groups apply correspondingly to divalent alkyl groups such as the groups alkanediyl $C_uH_{2u}$, $C_vH_{2v}$, $C_wH_{2w}$, $C_xH_{2x}$, $C_yH_{2y}$ and $C_zH_{2z}$ and bivalent alkenyl groups and alkynyl groups, such as the groups alkenediyl and alkynediyl, which thus can likewise be linear and branched. The double bonds and triple bonds in alkenediyl and alkynediyl groups can be present in any positions. In one embodiment of the invention, alkenediyl groups contain one double bond and alkynediyl groups contain one triple bond. Examples of divalent alkyl groups are —$CH_2$— (=methylene, —$CH_2$—$CH_2$—, —$CH_2$—$CH_2$—$CH_2$—, —$CH_2$—$CH_2$—$CH_2$—$CH_2$—, —CH($CH_3$)—, —C($CH_3$)$_2$—, —CH($CH_3$)—$CH_2$—, —$CH_2$—CH($CH_3$)—, —C($CH_3$)$_2$—$CH_2$—, —$CH_2$—C($CH_3$)$_2$—, examples of divalent alkenyl groups are —CH=CH—, —$CH_2$—CH=CH—, —CH=CH—$CH_2$—, —$CH_2$—CH=CH—$CH_2$—, —$CH_2$—$CH_2$—CH=CH—, —C($CH_3$)=C($CH_3$)—, and examples of divalent alkynyl groups are —C≡C—, —$CH_2$—C≡C—, —C≡C—$CH_2$—, —C($CH_3$)$_2$—C≡C—, —C≡C—C($CH_3$)$_2$—, —$CH_2$—C≡C—$CH_2$—, —$CH_2$—$CH_2$—C≡C—. If a number in a divalent group such as the number z in the group $C_zH_{2z}$, for example, is 0 (=zero), the two groups which are attached to the contemplated group, such as $C_zH_{2z}$, are directly connected to one another via a single bond.

The number of ring carbon atoms in a cycloalkyl group can be 3, 4, 5, 6 or 7. In one embodiment of the invention, the number of ring carbon atoms in a cycloalkyl group, independently of the number of ring carbon atoms in any other cycloalkyl group, is 3, 4, 5 or 6, in another embodiment 3, 4 or 5, in another embodiment 3 or 4, in another embodiment 3, in another embodiment 5, 6 or 7, in another embodiment 5 or 6, in another embodiment 6 or 7, in another embodiment 6. This applies accordingly to divalent cycloalkyl groups, i.e. cycloalkanediyl groups, which can be bonded to the adjacent groups via any one or two ring carbon atoms. Examples of cycloalkyl groups are cyclopropyl, cyclobutyl, cyclopentyl, cyclohexyl and cycloheptyl. Examples of divalent cycloalkyl groups are cyclopropane-1,1-diyl, cyclopropane-1,2-diyl, cyclobutane-1,3-diyl, cyclopentane-1,1-diyl, cyclopentane-1,2-diyl, cyclopentane-1,3-diyl, cyclohexane-1,1-diyl, cyclohexane-1,2-diyl, cyclohexane-1,3-diyl, cyclohexane-1,4-diyl, cycloheptane-1,4-diyl. Independently of one another and independently of any other substituents, cycloalkyl groups and cycloalkanediyl groups are optionally substituted by one or more identical or different ($C_1$-$C_4$)-alkyl substituents which can be located in any positions, i.e., cycloalkyl groups can be unsubstituted by alkyl substituents or substituted by alkyl substituents, for example by 1, 2, 3 or 4, or by 1 or 2, $(C_1-C_4)$-alkyl substituents, for example by methyl groups. Examples of alkyl-substituted cycloalkyl groups and cycloalkanediyl groups are 4-methylcyclohexyl, 4-tert-butylcyclohexyl or 2,3-dimethylcyclopentyl, 2,2-dimethylcyclopropane-1,1-diyl, 2,2-dimethylcyclopropane-1,2-diyl, 2,2-dimethylcyclopentane-1,3-diyl, 6,6-dimethylcycloheptane-1,4-diyl. Examples of cycloalkylalkyl groups, which can represent groups such as $(C_3-C_7)$-cycloalkyl-$C_zH_{2z}$—, for example, are cyclopropylmethyl, cyclobutylmethyl, cyclopentylmethyl, cyclohexylmethyl, cycloheptylmethyl, 1-cyclopropylethyl, 2-cyclopropylethyl, 1-cyclobutylethyl, 2-cyclobutylethyl, 2-cyclopentylethyl, 2-cyclohexylethyl, 2-cycloheptylethyl.

Independently of one another and independently of any other substituents, alkyl groups, divalent alkyl groups, alkenyl groups, divalent alkenyl groups, alkynyl groups, divalent alkynyl groups, cycloalkyl groups and divalent cycloalkyl groups may optionally be substituted by one or more fluorine substituents which can be located in any positions, i.e., these groups can be unsubstituted by fluorine substituents or substituted by fluorine substituents, for example by 1, 2, 3, 4, 5, 6, 7, 8, 9, 10, 11, 12 or 13, or by 1, 2, 3, 4, 5, 6, 7, 8 or 9, or by 1, 2, 3, 4, 5, 6 or 7, or by 1, 2, 3, 4 or 5, or by 1, 2 or 3, or by 1 or 2, fluorine substituents. Examples of such fluorine-substituted groups are trifluoromethyl, 2-fluoroethyl, 2,2,2-trifluoroethyl, pentafluoroethyl, 3,3,3-trifluoropropyl, 2,2,3,3,3-pentafluoropropyl, 4,4,4-trifluorobutyl, heptafluoroisopropyl, —CHF—, —CF$_2$—, —CF$_2$—CH$_2$—, —CH$_2$—CF$_2$—, —CF$_2$—CF$_2$—, —CF(CH$_3$)—, —C(CF$_3$)$_2$—, 1-fluorocyclopropyl, 2,2-difluorocyclopropyl, 3,3-difluorocyclobutyl, 1-fluorocyclohexyl, 4,4-difluorocyclohexyl, 3,3,4,4,5,5-hexafluorocyclohexyl, 2,2-difluorocyclopropane-1,2-diyl. Examples of alkyloxy groups in which the alkyl moiety is fluorine-substituted, are trifluoromethoxy, 2,2,2-trifluoroethoxy, pentafluoroethoxy and 3,3,3-trifluoropropoxy. In one embodiment of the invention, the total number of fluorine substituents and $(C_1-C_4)$-alkyl substituents, which independently of any other substituents are optionally present on cycloalkyl groups and cycloalkanediyl groups in the compounds of the formula I, is 1, 2, 3, 4, 5, 6, 7, 8, 9, 10 or 11, in another embodiment 1, 2, 3, 4, 5, 6, 7, 8 or 9, in another embodiment 1, 2, 3, 4 or 5, in another embodiment 1, 2, 3 or 4.

Groups like phenyl, naphthyl (=naphthalenyl) and residues of aromatic heterocycles which are optionally substituted by one or more substituents, can be unsubstituted or substituted, for example by 1, 2, 3, 4 or 5, or by 1, 2, 3 or 4, or by 1, 2 or 3, or by 1 or 2, or by 1, identical or different substituents which can be located in any positions. In one embodiment of the invention the total number of nitro substituents in a compound of the formula I is not greater than two. Aromatic nitrogen heterocycles which in the parent ring system carry a hydrogen atom on a ring nitrogen atom in a 5-membered ring, such as a pyrrole, imidazole, indole or benzimidazole ring, for example, can be substituted on the carbon atoms and/or on such ring nitrogen atoms. In one embodiment of the invention, substituents on such ring nitrogen atoms are chosen from $(C_1-C_4)$-alkyl groups, i.e. such ring nitrogen atoms in aromatic heterocycles carry a hydrogen atom or a $(C_1-C_4)$-alkyl substituent. When it is stated with respect to ring nitrogen atoms in aromatic heterocycles and any other heterocycles that they can carry a hydrogen atom or a substituent, such ring nitrogen atoms either carry a hydrogen atom or a substituent, or they do not carry a hydrogen atom or a substituent. Ring nitrogen atoms which carry a hydrogen atom or a substituent, occur in a nitrogen-containing aromatic 5-membered ring as is present in pyrrole, imidazole, indole or benzimidazole, for example, and in a non-aromatic ring including a saturated ring. Ring nitrogen atoms which do not carry a hydrogen atom or a substituent unless they are present in positively charged form, including any further ring nitrogen atoms in addition to ring nitrogen atoms which carry a hydrogen atom or a substituent, occur in an aromatic ring as is present in thiazole, imidazole, pyridine or benzimidazole, for example, and in a non-aromatic ring in which they are bridgehead atoms or are part of a double bond, and they occur as ring nitrogen atoms via which a ring is bonded. Suitable ring nitrogen atoms in aromatic heterocycles in the compounds of the formula I, such as the ring nitrogen atom in a pyridine ring, specifically a ring nitrogen atom in an aromatic heterocycle representing $R^2$, can also carry an oxy substituent $O^-$ and be present as an N-oxide, and such ring nitrogen atoms can also be present as quaternary salt, for example as N—$(C_1-C_4)$-alkyl salt such as N-methyl salt, wherein in one embodiment of the invention the counter anion in such quaternary salt is a physiologically acceptable anion which is derived from an acid that forms a physiologically acceptable salt. In monosubstituted phenyl groups, the substituent can be located in the 2-position, the 3-position or the 4-position. In disubstituted phenyl groups, the substituents can be located in 2,3-position, 2,4-position, 2,5-position, 2,6-position, 3,4-position or 3,5-position. In trisubstituted phenyl groups, the substituents can be located in 2,3,4-position, 2,3,5-position, 2,3,6-position, 2,4,5-position, 2,4,6-position or 3,4,5-position. Naphthyl can be 1-naphthyl (=naphthalen-1-yl) or 2-naphthyl (=naphthalen-2-yl). In monosubstituted 1-naphthyl groups, the substituent can be located in the 2-, 3-, 4-, 5-, 6-, 7- or 8-position. In monosubstituted 2-naphthyl groups, the substituent can be located in the 1-, 3-, 4-, 5-, 6-, 7- or 8-position. In disubstituted naphthyl groups, the substituents can likewise be located in any positions both in the ring via which the naphthyl group is bonded and/or in the other ring. This statement relating to the monovalent residues applies accordingly to the respective divalent residues, such as phenylene groups representing $R^2$, for example, which thus can likewise be unsubstituted or substituted, for example by 1, 2, 3 or 4, or by 1, 2 or 3, or by 1 or 2, or by 1, identical or different substituents which can be located in any positions.

In aromatic heterocycles, which may be designated as heteroaryl and heteroarylene groups, as well as in all other heterocyclic rings and non-aromatic heterocyclic groups, the ring heteroatoms are generally chosen from N, O and S, where N includes ring nitrogen atoms which carry a hydrogen atom or a substituent as well as ring nitrogen atoms which do not carry a hydrogen atom or a substituent. Ring heteroatoms can be located in any positions, provided that the heterocyclic system is known in the art and is stable and suitable as a subgroup for the desired purpose of the compound of the formula I such as use as a drug substance. In one embodiment of the invention, two ring oxygen atoms cannot be present in adjacent ring positions of any heterocycle, in another embodiment two ring heteroatoms chosen from oxygen and sulfur cannot be present in adjacent ring positions of any heterocycle. Saturated rings do not contain a double bond within the ring. Unsaturated ring systems can be aromatic or partially unsaturated including partially aromatic, in which latter case one ring in a bicyclic ring system is aromatic and the ring system is bonded via an atom in the non-aromatic ring. Depending on the respective group, unsaturated rings can contain one, two, three, four or five double bonds within the ring. Aromatic groups contain a cyclic system of six or ten delocalized pi electrons in the ring. Depending on the respective group, saturated and non-aromatic unsaturated heterocyclic rings, including Het and non-aromatic groups representing R³, can be 3-membered, 4-membered, 5-membered, 6-membered, 7-membered, 8-membered, 9-membered or 10-membered. In one embodiment of the invention, aromatic heterocyclic rings are 5-membered or 6-membered monocyclic rings or 8-membered, 9-membered or 10-membered bicyclic rings, in another embodiment 5-membered or 6-membered monocyclic rings or 9-membered or 10-membered bicyclic rings, in another embodiment 5-membered or 6-membered monocyclic rings, where the 8-membered, 9-membered or 10-membered bicyclic rings are composed of two fused 5-membered rings, a 5-membered ring and a 6-membered ring which are fused to one another, and two fused 6-membered rings, respectively. In bicyclic aromatic heterocyclic groups, one or both rings can contain hetero ring members, and one or both rings can be aromatic. In general, bicyclic ring systems containing an aromatic ring and a non-aromatic ring are regarded as aromatic when they are bonded via a carbon atom in the aromatic ring, and as non-aromatic when they are bonded via a carbon atom in the non-aromatic ring. Unless stated otherwise, heterocyclic groups including aromatic heterocyclic groups can be bonded via any suitable ring carbon atom and, in the case of nitrogen heterocycles, via any suitable ring nitrogen atom. In one embodiment of the invention, an aromatic heterocyclic group in a compound of the formula I, independently of any other aromatic heterocyclic group, is bonded via a ring carbon atom, in another embodiment via a ring nitrogen atom. Depending on the definition of the respective heterocyclic group, in one embodiment of the invention the number of ring heteroatoms which can be present in a heterocyclic group, independently of the number of ring heteroatoms in any other heterocyclic group, is 1, 2, 3 or 4, in another embodiment 1, 2 or 3, in another embodiment 1 or 2, in another embodiment 1, where the ring heteroatoms can be identical or different. Heterocyclic groups which are optionally substituted, can independently of any other heterocyclic group be unsubstituted or substituted by one or more identical or different substituents, for example by 1, 2, 3, 4 or 5, or by 1, 2, 3 or 4, or by 1, 2 or 3, or by 1 or 2, or by 1 substituents, which are indicated in the definition of the respective group. Substituents on heterocyclic groups can be located in any positions. For example, in a pyridin-2-yl group substituents can be located in the 3-position and/or 4-position and/or 5-position and/or 6-position, in a pyridin-3-yl group substituents can be located in the 2-position and/or 4-position and/or 5-position and/or 6-position and in a pyridin-4-yl group substituents can be located in the 2-position and/or 3-position and/or 5-position and/or 6-position.

Examples of parent heterocycles, from which heterocyclic groups including aromatic heterocyclic groups, saturated heterocyclic groups and non-aromatic unsaturated heterocyclic groups can be derived, are azete, oxete, pyrrole, furan, thiophene, imidazole, pyrazole, [1,3]dioxole, oxazole (=[1,3]oxazole), isoxazole (=[1,2]oxazole), thiazole (=[1,3]thiazole), isothiazole (=[1,2]thiazole), [1,2,3]triazole, [1,2,4]triazole, [1,2,4]oxadiazole, [1,3,4]oxadiazole, [1,2,4]thiadiazole, [1,3,4]thiadiazole, tetrazole, pyridine, pyran, thiopyran, pyridazine, pyrimidine, pyrazine, [1,3]oxazine, [1,4]oxazine, [1,3]thiazine, [1,4]thiazine, [1,2,3]triazine, [1,3]dithiine, [1,4]dithiine, [1,2,4]triazine, [1,3,5]triazine, [1,2,4,5]tetrazine, azepine, [1,3]diazepine, [1,4]diazepine, [1,3]oxazepine, [1,4]oxazepine, [1,3]thiazepine, [1,4]thiazepine, azocine, azecine, cyclopenta[b]pyrrole, 2-azabicyclo[3.1.0]hexane, 3-azabicyclo[3.1.0]hexane, 2-oxa-5-azabicyclo[2.2.1]heptane, indole, isoindole, benzothiophene, benzofuran, [1,3]benzodioxole (=1,2-methylenedioxybenzene), [1,3]benzoxazole, [1,3]benzothiazole, benzimidazole, thieno[3,2-c]pyridine, chromene, isochromene, [1,4]benzodioxine, [1,4]benzoxazine, [1,4]benzothiazine, quinoline, isoquinoline, cinnoline, quinazoline, quinoxaline, phthalazine, thienothiophene, [1,8]naphthyridine and other naphthyridines, pteridine, and the respective saturated and partially unsaturated heterocycles in which one or more, for example one, two, three, four or all double bonds within the ring system including double bonds in the aromatic ring are replaced with single bonds, such as azetidine, oxetane, pyrrolidine, tetrahydrofuran, tetrahydrothiophene, imidazolidine, oxazolidine, thiazolidine, dihydropyridine, piperidine, tetrahydropyran, piperazine, morpholine, thiomorpholine, azepane, chroman, isochroman, [1,4]benzodioxane (=1,2-ethylenedioxybenzene), 2,3-dihydrobenzofuran, 1,2,3,4-tetrahydroquinoline, 1,2,3,4-tetrahydroisoquinoline, for example.

Examples of residues of aromatic heterocycles, which can occur in the compounds of the formula I, are thiophenyl (=thienyl) including thiophen-2-yl and thiophen-3-yl, pyridinyl (=pyridyl) including pyridin-2-yl (=2-pyridyl), pyridin-3-yl (=3-pyridyl) and pyridin-4-yl (=4-pyridyl), imidazolyl including, for example, 1H-imidazol-1-yl, 1H-imidazol-2-yl, 1H-imidazol-4-yl and 1H-imidazol-5-yl, [1,2,4]triazolyl including 1H-[1,2,4]-triazol-1-yl and 4H-[1,2,4]-triazol-3-yl, tetrazolyl including 1H-tetrazol-1-yl and 1H-tetrazol-5-yl, quinolinyl (=quinolyl) including quinolin-2-yl, quinolin-3-yl, quinolin-4-yl, quinolin-5-yl, quinolin-6-yl, quinolin-7-yl and quinolin-8-yl, which all are optionally substituted as indicated in the definition of the respective group. Examples of residues of saturated and partially unsaturated heterocycles, which can occur in the compounds of the formula I, are azetidinyl, pyrrolidinyl including pyrrolidin-1-yl, pyrrolidin-2-yl and pyrrolidin-3-yl, 2,5-dihydro-1H-pyrrolyl, piperidinyl including piperidin-1-yl, piperidin-2-yl, piperidin-3-yl and piperidin-4-yl, 1,2,3,4-tetrahydropyridinyl, 1,2,5,6-tetrahydropyridinyl, 1,2-dihydropyridinyl, azepanyl, azocanyl, azecanyl, octahydrocyclopenta[b]pyrrolyl, 2,3-dihydrobenzofuranyl including 2,3-dihydrobenzofuran-7-yl, 2,3-dihydro-1H-indolyl, octahydro-1H-indolyl, 2,3-dihydro-1H-isoindolyl, octahydro-1H-isoindolyl, 1,2-dihydroquinolinyl, 1,2,3,4-tetrahydroquinolinyl, decahydroquinolinyl, 1,2-dihydroisoquinolinyl, 1,2,3,4-tetrahydroisoquinolinyl, 1,2,3,4-tetrahydroisoquinolinyl, decahydroisoquinolinyl, decahydroisoquinolinyl, 4,5,6,7-tetrahydrothieno[3,2-c]pyridinyl, pyrazolidinyl, imidazolidinyl, hexahydropyrimidinyl, 1,2-dihydropyrimidinyl, piperazinyl, [1,3]diazepanyl, [1,4]diazepanyl, oxazolidinyl, [1,3]oxazinanyl, [1,3]oxazepanyl, morpholinyl including morpholin-2-yl, morpholin-3-yl and morpholin-4-yl, [1,4]oxazepanyl, thiazolidinyl, [1,3]thiazinanyl, thiomorpholinyl including thiomorpholin-2-yl, thiomorpholin-3-yl and thiomorpholin-4-yl, 3,4-dihydro-2H-[1,4]thiazinyl, [1,3]thiazepanyl, [1,4]thiazepanyl, [1,4]thiazepanyl, oxetanyl, tetrahydrofuranyl, tetrahydrothienyl, isoxazolidinyl, isothiazolidinyl, oxazolidinyl, [1,2,4]-oxadiazolidinyl, [1,2,4]-thiadiazolidinyl, [1,2,4]triazolidinyl, [1,3,4]oxadiazolidinyl, [1,3,4]thiadiazolidinyl, [1,3,4]triazolidinyl, 2,3-dihydrofuranyl, 2,5-dihydrofuranyl, 2,3-dihydrothienyl, 2,5-dihydrothienyl, 2,3-dihydropyrrolyl, 2,3-dihydroisoxazolyl, 4,5-dihydroisoxazolyl, 2,5-dihydroisoxazolyl, 2,3-dihydroisothiazolyl, 4,5-dihydroisothiazolyl, 2,5-dihydroisothiazolyl, 2,3-dihydropyrazolyl, 4,5-dihydropyrazolyl, 2,5-dihydropyrazolyl, 2,3-dihydrooxazolyl, 4,5-dihydrooxazolyl, 2,5-dihydrooxazolyl, 2,3-dihydrothiazolyl, 4,5-dihydrothiazolyl, 2,5-dihydrothiazolyl, 2,3-dihydroimidazolyl, 4,5-dihydroimidazolyl, 2,5-dihydroimidazolyl, tetrahydropyridazinyl, tetrahydropyrimidinyl, tetrahydropyrazinyl, tetrahydro[1,3,5]triazinyl, [1,3]dithianyl, tetrahydropyranyl, tetrahydrothiopyranyl, [1,3]dioxolanyl, 3,4,5,6-tetrahydropyridinyl, 4H-[1,3]thiazinyl, 1,1-dioxo-2,3,4,5-tetrahydrothienyl, 2-azabicyclo[3.1.0]hexyl including 2-azabicyclo[3.1.0]hex-2-yl, 3-azabicyclo[3.1.0]hexyl including 3-azabicyclo[3.1.0]hex-3-yl, 2-oxa-5-azabicyclo[2.2.1]-heptyl including 2-oxa-5-azabicyclo[2.2.1]-hept-5-yl, which all are bonded via any suitable ring carbon atom or ring nitrogen atom and are optionally substituted as indicated in the definition of the respective group.

Halogen is fluorine, chlorine, bromine or iodine. In one embodiment of the invention, any halogen in a compound of the formula I is independently of any other halogen chosen from fluorine, chlorine and bromine, in another embodiment from fluorine and chlorine.

When an oxo group is bonded to a carbon atom, it replaces two hydrogen atoms on a carbon atom of the parent system. Thus, if a $CH_2$ group in a chain or a ring is substituted by oxo, i.e. by a doubly bonded oxygen atom, it becomes a $C(O)$ ($=C(=O)$) group. Evidently, an oxo group cannot occur as a substituent on a carbon atom in an aromatic ring such as in a phenyl group, for example. When a ring sulfur atom in a heterocyclic group can carry one or two oxo groups, it is a non-oxidized sulfur atom S in case it does not carry any oxo group, or it is an S(O) group (=sulfoxide group, S oxide group) in case it carries one oxo group, or it is an $S(O)_2$ group (=sulfone group, S,S dioxide group) in case it carries two oxo groups.

The present invention includes all stereoisomeric forms of the compounds of the formula I and their salts and solvates. With respect to each chiral center, independently of any other chiral center, the compounds of the formula I can be present in S configuration or substantially S configuration, or in R configuration or substantially R configuration, or as a mixture of the S isomer and the R isomer in any ratio. The invention includes all possible enantiomers and diastereomers and mixtures of two or more stereoisomers, for example mixtures of enantiomers and/or diastereomers, in all ratios. Thus, compounds according to the invention which can exist as enantiomers can be present in enantiomerically pure form, both as levorotatory and as dextrorotatory antipodes, and in the form of mixtures of the two enantiomers in all ratios including racemates. In the case of an E/Z isomerism, or cis/trans isomerism, for example on double bonds or rings such as cycloalkyl rings, the invention includes both the E form and Z form, or the cis form and the trans form, as well as mixtures of these forms in all ratios. In one embodiment of the invention, a compound which can occur in two or more stereoisomeric forms is a pure, or substantially pure, individual stereoisomer. The preparation of individual stereoisomers can be carried out, for example, by separation of a mixture of isomers by customary methods, for example by chromatography or crystallization, by the use of stereochemically uniform starting materials in the synthesis, or by stereoselective synthesis. Optionally, a derivatization can be carried out before a separation of stereoisomers. The separation of a mixture of stereoisomers can be carried out at the stage of the compound of the formula I or at the stage of a starting material or an intermediate during the synthesis. The present invention also includes all tautomeric forms of the compounds of the formula I and their salts and solvates.

In case the compounds of the formula I contain one or more acidic and/or basic groups, i.e. salt-forming groups, the invention also includes their corresponding physiologically or toxicologically acceptable salts, i.e. non-toxic salts, in particular their pharmaceutically acceptable salts.

The present invention includes all solvates of compounds of the formula I, for example hydrates or adducts with alcohols such as $(C_1-C_4)$-alkanols, active metabolites of the compounds of the formula I, and also prodrugs and derivatives of the compounds of the formula I which in vitro may not necessarily exhibit pharmacological activity but which in vivo are converted into pharmacologically active compounds, for example esters or amides of carboxylic acid groups.

The alkanediyl, alkenediyl and alkynediyl groups occurring in the group X can be linear or branched, as already indicated with respect to such groups in general, and these groups as well as cycloalkanediyl groups representing X can be bonded to the adjacent groups, i.e. to the group $R^1O—C(O)$ and the group Y or, in the case of the group alkanediyloxy, to the oxygen atom of the alkanediyloxy group, via any positions. The adjacent groups can be bonded to the same carbon atom or to different carbon atoms in the group X. In one embodiment, the chain of carbon atoms in an alkanediyl, alkenediyl and alkynediyl groups occurring in the group X which directly connects the group $R^1O—C(O)$ to the group Y or, in the case of the group alkanediyloxy, to the oxygen atom of the alkanediyloxy group, consists of 1, 2, 3 or 4 carbon atoms, in another embodiment of 1, 2 or 3 carbon atoms, in another embodiment of 1 or 2 carbon atoms, in another embodiment of 1 carbon atom. In the case of a cycloalkanediyl group representing X, in one embodiment the groups $R^1O—C(O)$ and Y are bonded to two ring carbon atoms which are in 1,2-position, 1,3-position or 1,4-position with respect to each other, in another embodiment in 1,2-position or 1,3-position with respect to each other, in another embodiment in 1,2-position with respect to each other, in another embodiment in 1,4-position with respect to each other. In one embodiment, X is chosen from $(C_1-C_6)$-alkanediyl, $(C_2-C_6)$-alkenediyl, $(C_3-C_7)$-cycloalkanediyl and $(C_1-C_6)$-alkanediyloxy, in another embodiment from $(C_1-C_6)$-alkanediyl, $(C_2-C_6)$-alkenediyl and $(C_1-C_6)$-alkanediyloxy, in another embodiment from $(C_1-C_6)$-alkanediyl, $(C_3-C_7)$-cycloalkanediyl and $(C_1-C_6)$-alkanediyloxy, in one embodiment from $(C_1-C_6)$-alkanediyl and $(C_1-C_6)$-alkanediyloxy, in another embodiment from $(C_1-C_6)$-alkanediyl, $(C_2-C_6)$-alkenediyl, $(C_2-C_6)$-alkynediyl and $(C_3-C_7)$-cycloalkanediyl, in another embodiment from $(C_1-C_6)$-alkanediyl, $(C_2-C_6)$-alkenediyl and $(C_3-C_7)$-cycloalkanediyl, in another embodiment from $(C_1-C_6)$-alkanediyl and $(C_2-C_6)$-alkenediyl, in another embodiment X is $(C_1-C_6)$-alkanediyl, in another embodiment X is $(C_2-C_6)$-alkenediyl, in another embodiment X is $(C_3-C_7)$-cycloalkanediyl, and in another embodiment X is $(C_1-C_6)$-alkanediyloxy, which all are optionally substituted as indicated. In one embodiment a $(C_1-C_6)$-alkanediyl group occurring in X is a $(C_1-C_4)$-alkanediyl group, in another embodiment a $(C_1-C_3)$-alkanediyl group, in another embodiment a $(C_1-C_2)$-alkanediyl group. In one embodiment, the $(C_2-C_6)$-alkenediyl and $(C_2-C_6)$-alkynediyl groups representing X are $(C_2-C_4)$-alkenediyl and $(C_2-C_4)$-alkynediyl groups, in another embodiment $(C_2-C_3)$-alkenediyl and $(C_2-C_3)$-alkynediyl groups. In one embodiment, a $(C_3-C_7)$-cycloalkanediyl group representing X is a $(C_3-C_6)$-cycloalkanediyl group, in another embodiment a $(C_3-C_4)$-cycloalkanediyl group, in another embodiment a cyclopropanediyl group, in another embodiment a cyclohexanediyl group. Examples of groups X from any one or more of which the respective group representing X can be chosen in the aforementioned embodiments, or from any one or more of which X can be chosen in another embodiment of the invention, are methylene, —CH($CH_3$)— (ethane-1,1-diyl), —$CH_2$—$CH_2$— (ethane-1,2-diyl, 1,2-ethylene), —C($CH_3$)$_2$— (1-methylethane-1,1-diyl), —$CH_2$—$CH_2$—

CH$_2$— (propane-1,3-diyl, 1,3-propylene), —CH$_2$—CH(CH$_3$)— and —CH(CH$_3$)—CH$_2$— (propane-1,2-diyl, 1,2-propylene), which exemplify the group (C$_1$-C$_6$)-alkanediyl, —CH=CH— (ethene-1,2-diyl), —CH=CH—CH$_2$— and —CH$_2$—CH=CH— (prop-1-ene-1,3-diyl and prop-2-ene-1,3-diyl) and —CH=C(CH$_3$)— and —C(CH$_3$)=CH— (prop-1-ene-1,2-diyl) which exemplify the group (C$_2$-C$_6$)-alkenediyl, —C≡C— (ethynediyl) and —CH$_2$—C≡C and —C≡C—CH$_2$— (prop-1-yne-1,3-diyl and prop-2-yne-1,3-diyl) which exemplify the group (C$_2$-C$_6$)-alkynediyl, cyclopropane-1,1-diyl, cyclopropane-1,2-diyl and cyclohexane-1,4-diyl which exemplify the group (C$_3$-C$_7$)-cycloalkanediyl, —CH$_2$—O— (methyleneoxy), —CH$_2$—CH$_2$—O— (ethane-1,2-diyloxy), —CH(CH$_3$)—O— (ethane-1,1-diyloxy), —C(CH$_3$)$_2$—O— (1-methylethane-1,1-diyloxy), —CH$_2$—CH$_2$—CH$_2$—O— (propane-1,3-diyl-oxy) and —CH$_2$—CH$_2$—CH$_2$—CH$_2$—O— (butane-1,4-diyloxy) which exemplify the group (C$_1$-C$_6$)-alkanediyloxy, all of which are optionally substituted as indicated. Thus, in one embodiment X is chosen from —CH$_2$—O—, —CH$_2$—CH$_2$—O—, —CH(CH$_3$)—O— and —C(CH$_3$)$_2$—O—, in another embodiment from —CH$_2$—O—, —CH$_2$—CH$_2$—O— and —CH(CH$_3$)—O—, in another embodiment from —CH$_2$—O— and —CH(CH$_3$)—O—, and in another embodiment X is —CH$_2$—O—, all of which are optionally substituted as indicated, and in which the oxygen atom is bonded to the group Y. In one embodiment, the number of substituents which are optionally present in X, is 1, 2, 3 or 4, in another embodiment 1, 2 or 3, in another embodiment 1 or 2, in another embodiment 1, and in another embodiment the group X is not substituted by substituents chosen from fluorine and hydroxy. In one embodiment, the number of hydroxy substituents in X is not greater than 2, in another embodiment not greater than 1. In one embodiment, no more than one hydroxy substituent is present on an individual carbon atom in X. In one embodiment, hydroxy substituents are not present on carbon atoms which are part of a double bond in the group (C$_2$-C$_6$)-alkenediyl. In one embodiment, hydroxy substituents are not present on the carbon atom in the group (C$_1$-C$_6$)-alkanediyloxy which is bonded to the oxygen atom, in another embodiment no substituents are present on the carbon atom in the group (C$_1$-C$_6$)-alkanediyloxy which is bonded to the oxygen atom, i.e. in this latter embodiment all carbon atoms which are not linked to the said oxygen atom are optionally substituted by one or more identical or different substituents chosen from fluorine and hydroxy. The double bond in the group (C$_2$-C$_6$)-alkenediyl can have E configuration or Z configuration. In one embodiment it has E configuration, in another embodiment it has Z configuration.

In one embodiment of the invention, the group R$^1$ is chosen from hydrogen and (C$_1$-C$_4$)-alkyl, in another embodiment R$^1$ is chosen from hydrogen, methyl, ethyl, n-propyl, n-butyl and isopropyl, in another embodiment from hydrogen, methyl and ethyl, in another embodiment R$^1$ is hydrogen, in another embodiment R$^1$ is (C$_1$-C$_4$)-alkyl, in another embodiment R$^1$ is methyl.

In one embodiment of the invention, the number of ring heteroatoms in an aromatic heterocycle representing Y is 1 or 2, in another embodiment it is 1. In one embodiment of the invention, Y is chosen from phenylene and a divalent residue of an aromatic, 6-membered monocyclic heterocycle which comprises 1, 2 or 3 ring nitrogen atoms, in another embodiment 1 or 2 ring nitrogen atoms, in another embodiment 1 ring nitrogen atom, where one of the ring nitrogen atoms can carry a substituent R$^4$ which is oxy, i.e. where one of the ring nitrogen atoms can be oxidized to the N-oxide, and where the phenylene and divalent residue of an aromatic heterocycle are optionally substituted on one or more ring carbon atoms by identical or different substituents R$^5$. In another embodiment, Y is phenylene, where the phenylene is optionally substituted on one or more ring atoms by identical or different substituents R$^5$, and in another embodiment Y is pyridinediyl, where the ring nitrogen atom can carry a substituent R$^4$ which is oxy, i.e. where the ring nitrogen atom can be oxidized to the N-oxide, and where the pyridinediyl is optionally substituted on one or more ring carbon atoms by identical or different substituents R$^5$. In another embodiment, Y is a divalent residue of an aromatic 5-membered heterocycle which comprises 1, 2 or 3 identical or different ring heteroatoms chosen from N, O and S, where one of the ring nitrogen atoms can carry a hydrogen atom or a substituent R$^4$, and where the divalent residue of an aromatic heterocycle is optionally substituted on one or more ring carbon atoms by identical or different substituents R$^5$. In one embodiment, a divalent residue of an aromatic heterocyclic group representing Y is chosen from furandiyl, thiophenediyl, oxazolediyl, thiazolediyl, pyridinediyl, pyridazinediyl, pyrimidinediyl and pyrazinediyl, in another embodiment from furandiyl, thiophenediyl, thiazolediyl, pyridinediyl, pyridazinediyl, pyrimidinediyl and pyrazinediyl, in another embodiment from furandiyl, thiophenediyl, pyridinediyl, pyridazinediyl, pyrimidinediyl and pyrazinediyl, in another embodiment from furandiyl, thiophenediyl, pyridinediyl and pyrimidinediyl, in another embodiment from furandiyl, thiophenediyl and pyridinediyl, which are all optionally substituted as indicated with respect to Y.

The ring carbon atoms via which the phenylene group and the divalent residue of an aromatic heterocycle representing Y are bonded to the oxazolopyrimidine ring and to the group X, can be in any positions. A phenylene group representing Y can be 1,2-phenylene, i.e. the oxazolopyrimidine ring and the group X can be bonded in 1,2-position, or ortho position, with respect to each another, it can be 1,3-phenylene, i.e. the oxazolopyrimidine ring and the group X can be bonded in 1,3-position, or meta position, with respect to each another, and it can be 1,4-phenylene, i.e. the oxazolopyrimidine ring and the group X can be bonded in 1,4-position, or para position, with respect to each another. In one embodiment, a phenylene group representing Y is chosen from 1,3-phenylene and 1,4-phenylene, in another embodiment it is 1,3-phenylene, and in another embodiment it is 1,4-phenylene, which all are optionally substituted as indicated with respect to Y. In one embodiment, Y is chosen from one or more of the groups phenylene, furan-2,5-diyl, thiophene-2,4-diyl, thiophene-2,5-diyl, pyridine-2,4-diyl, pyridine-2,5-diyl, pyridine-3,5-diyl, pyridine-2,6-diyl and pyrimidine-2,5-diyl, in another embodiment from the groups furan-2,5-diyl, thiophene-2,4-diyl, thiophene-2,5-diyl, pyridine-2,4-diyl, pyridine-2,5-diyl, pyridine-3,5-diyl, pyridine-2,6-diyl and pyrimidine-2,5-diyl, in another embodiment from pyridine-2,4-diyl, pyridine-2,5-diyl, pyridine-3,5-diyl and pyridine-2,6-diyl, in another embodiment from phenylene, pyridine-2,4-diyl, pyridine-2,5-diyl, pyridine-3,5-diyl and pyridine-2,6-diyl, which all are optionally substituted as indicated with respect to Y. In one embodiment, the number of substituents R$^5$ which can be optionally present on ring carbon atoms in Y, is 1, 2, 3, 4 or 5, in another embodiment 1, 2, 3 or 4, in another embodiment 1, 2 or 3, in another embodiment 1 or 2, in another embodiment 1. Ring carbon atoms in Y which do not carry a substituent R$^5$, carry a hydrogen atom.

In one embodiment of the invention, the substituents R$^5$ which are optionally present on the group Y, are chosen from halogen, hydroxy, (C$_1$-C$_4$)-alkyl-, (C$_3$-C$_5$)-cycloalkyl-C$_z$H$_{2z}$—, (C$_1$-C$_4$)-alkyloxy-, (C$_1$-C$_4$)-alkyl-S(O)$_m$—, amino, nitro and cyano, in another embodiment from halogen, hydroxy, $(C_1-C_4)$-alkyl-, $(C_3-C_5)$-cycloalkyl-$C_zH_{2z}$—, $(C_1-C_4)$-alkyloxy-, amino and cyano-, in another embodiment from halogen, hydroxy, $(C_1-C_4)$-alkyl- and $(C_1-C_4)$-alkyloxy-, in another embodiment from fluorine, chlorine, hydroxy, $(C_1-C_4)$-alkyl- and $(C_1-C_4)$-alkyloxy-, in another embodiment from fluorine, chlorine and $(C_1-C_4)$-alkyl-, and in another embodiment they are $(C_1-C_4)$-alkyl substituents, where z is chosen from 0, 1 and 2.

In one embodiment, 1, 2 or 3 of the substituents $R^5$, in another embodiment 1 or 2 of the substituents $R^5$, and in another embodiment 1 of the substituents $R^5$, which are optionally present on the group Y, are defined as in the general definition of $R^5$ and thus are chosen from halogen, hydroxy, $(C_1-C_4)$-alkyl-, $(C_3-C_5)$-cycloalkyl-$C_zH_{2z}$—, $(C_1-C_4)$—alkyloxy-, $(C_1-C_4)$-alkyl-$S(O)_m$—, amino, nitro, cyano, hydroxycarbonyl, $(C_1-C_4)$-alkyloxycarbonyl, aminocarbonyl and aminosulfonyl, and any further substituents $R^5$ which are optionally present on the group Y, for example 1, 2 or 3 further substituents $R^5$, or 1 or 2 further substituents $R^5$, or 1 further substituent $R^5$, are chosen from halogen, hydroxy, $(C_1-C_4)$-alkyl-, $(C_3-C_5)$-cycloalkyl-$C_zH_{2z}$—, $(C_1-C_4)$-alkyloxy-, $(C_1-C_4)$—alkyl-$S(O)_m$—, amino, nitro and cyano, where all alkyl groups independently of each other are optionally substituted by one or more fluorine substituents as generally applies to alkyl groups. In one embodiment, the said substituents $R^5$ which are optionally present on the group Y and which in the aforementioned embodiment are defined as in the general definition of $R^5$, for example 1 or 2 such substituents $R^5$, or 1 such substituent $R^5$, are chosen from halogen, hydroxy, $(C_1-C_4)$-alkyl-, $(C_3-C_5)$-cycloalkyl-$C_zH_{2z}$—, $(C_1-C_4)$—alkyloxy-, $(C_1-C_4)$-alkyl-$S(O)_m$—, amino and cyano, where z is chosen from 0, 1 and 2. In one embodiment, the said substituents $R^5$ which are optionally present on the group Y and which in the aforementioned embodiment are defined as in the general definition of $R^5$, for example 1 or 2 such substituents $R^5$, or 1 such substituent $R^5$, are not located on ring carbon atoms within the group Y which are adjacent to the atom via which the group Y is bonded to the oxazolopyrimidine ring depicted in formula I. In one embodiment, the said further substituents $R^5$ which are optionally present on the group Y, for example 1, 2 or 3 further substituents $R^5$, or 1 or 2 further substituents $R^5$, or 1 further substituent $R^5$, are chosen from halogen, hydroxy, $(C_1-C_4)$-alkyl-, $(C_1-C_4)$-alkyloxy-, amino, cyano, in another embodiment from halogen, hydroxy, $(C_1-C_4)$-alkyl- and $(C_1-C_4)$-alkyloxy-, in another embodiment from halogen, $(C_1-C_4)$-alkyl- and $(C_1-C_4)$-alkyloxy-, in another embodiment from halogen and $(C_1-C_4)$-alkyloxy-, in another embodiment from halogen and $(C_1-C_4)$-alkyl-, where in all these embodiments all alkyl groups independently of each other are optionally substituted by one or more fluorine substituents.

In one embodiment of the invention, the number z is chosen from 0 and 1, in another it is 0, in another embodiment it is 1.

The invention provides all compounds of the formula I wherein any one or more structural elements such as groups, substituents and numbers are defined as in any of the specified embodiments or definitions of the elements or have any one or more of the specific meanings which are mentioned herein as examples of elements, wherein all combinations of one or more specified embodiments and/or definitions and/or specific meanings of the elements are a subject of the present invention. Also with respect to all such compounds of the formula I, all their stereoisomeric forms and mixtures of stereoisomeric forms in any ratio, and their physiologically acceptable salts, and the physiologically acceptable solvates of any of them, are a subject of the present invention.

A further embodiment relates to compounds of the formula I in which one or more radicals have the following meanings:

A is selected from the group consisting of a bond, —$CH_2$—, NH, O and S;

X is selected from the group consisting of $(C_1-C_6)$-alkanediyl, $(C_2-C_6)$-alkenediyl, $(C_2-C_6)$-alkynediyl, $(C_3-C_7)$-cycloalkanediyl, $(C_1-C_6)$-alkanediyloxy and $(C_3-C_7)$-cycloalkanediyloxy; all of which are optionally substituted by one or more identical or different substituents selected from the group consisting of fluorine and hydroxyl, where the oxygen atom of the $(C_1-C_6)$-alkanediyloxy and $(C_3-C_7)$-cycloalkanediyloxy groups is attached to group Y;

Y is selected from the group consisting of phenylene and a bivalent radical of an aromatic 5-membered or 6-membered monocyclic heterocycle which contains 1, 2 or 3 identical or different ring heteroatoms selected from the group consisting of N, O and S, where one of the ring nitrogen atoms may carry a hydrogen atom or a substituent $R^4$ and where the phenylene and the bivalent radical of an aromatic heterocycle are optionally substituted at one or more ring carbon atoms by identical or different substituents $R^5$;

$R^1$ is selected from the group consisting of hydrogen, $(C_1-C_4)$-alkyl and $(C_3-C_7)$—cycloalkyl-$C_zH_{2z}$—, where z is selected from the group consisting of 0, 1 and 2;

$R^2$ is selected from the group consisting of $(C_1-C_6)$-alkyl, $(C_3-C_5)$-cycloalkyl-$C_xH_{2x}$— and $Het^1$-$C_nH_{2n}$—, where x and n are selected from the group consisting of 0, 1 and 2;

$R^3$ is selected from the group consisting of $(C_1-C_6)$-alkyl, where the alkyl radical is optionally substituted by one or more fluorine atoms, $(C_2-C_6)$-alkenyl, $(C_2-C_6)$-alkynyl, $(C_3-C_7)$-cycloalkyl-$C_uH_{2u}$— and $Het^2$-$C_vH_{2v}$—, where u and v are selected from the group consisting of 1 and 2, or $R^3$ is a radical of a saturated or unsaturated 3-membered to 10-membered monocyclic or bicyclic ring which contains 0, 1, 2, 3 or 4 identical or different ring heteroatoms selected from the group consisting of N, O and S, where one or two of the ring nitrogen atoms may carry a hydrogen atom or a $(C_1-C_4)$-alkyl substituent and one or two of the ring sulfur atoms may carry one or two oxo groups and where the radical of a ring is optionally substituted at one or more ring carbon atoms by identical or different substituents $R^{31}$;

$R^4$ is selected from the group consisting of $(C_1-C_4)$-alkyl, $(C_3-C_7)$-cycloalkyl-$C_wH_{2w}$— and oxy, where w is selected from the group consisting of 0, 1 and 2;

$R^5$ is selected from the group consisting of halogen, hydroxyl, $(C_1-C_4)$-alkyl-, $(C_3-C_6)$-cycloalkyl-$C_zH_{2z}$—, $(C_1-C_4)$-alkyloxy, $(C_1-C_4)$-alkyl-$S(O)_m$—, amino, nitro, cyano, hydroxycarbonyl, $(C_1-C_4)$-alkyloxycarbonyl, aminocarbonyl and aminosulfonyl, where z is selected from the group consisting of 0, 1 and 2;

$R^{31}$ is selected from the group consisting of halogen, hydroxyl, $(C_1-C_4)$-alkyl, $(C_1-C_4)$-alkyloxy, $(C_3-C_7)$-cycloalkyl, oxo, $(C_1-C_4)$-alkyl-$S(O)_m$—, amino, $(C_1-C_4)$-alkylamino, di$((C_1-C_4)$-alkyl)amino, $(C_1-C_4)$-alkylcarbonylamino, $(C_1-C_4)$-alkylsulfonylamino, nitro, cyano, $(C_1-C_4)$-alkylcarbonyl, aminosulfonyl, $(C_1-C_4)$-alkylaminosulfonyl and di$((C_1-C_4)$-alkyl)aminosulfonyl;

$Het^1$ is a radical of a saturated 4-membered to 6-membered monocyclic saturated heterocycle which contains 1 or 2 oxygen atoms and which is attached via a ring carbon atom, and where the radical of a heterocycle is optionally substituted by one or more identical or different substituents selected from the group consisting of fluorine and $(C_1-C_4)$-alkyl;

$Het^2$ is a radical of a saturated 4-membered to 7-membered monocyclic heterocycle which contains 1 or 2 identical or different ring heteroatoms selected from the group consisting of N, O and S and which is attached via a ring carbon atoms, where the radical of a heterocycle is optionally substituted by one or more identical or different substituents selected from the group consisting of fluorine and $(C_1-C_4)$-alkyl;

m is selected from the group consisting of 0, 1 and 2.

A further embodiment relates to compounds of the formula I in which one or more radicals have the following meanings:

A is a bond, —$CH_2$—, NH, O or S;

X is $(C_1-C_6)$-alkanediyloxy, where the oxygen atom of the $(C_1-C_6)$-alkanediyloxy group is attached to the group Y;

Y is phenylene, where the phenylene is optionally substituted at one or more ring carbon atoms by identical or different substituents $R^5$;

$R^1$ is hydrogen or $(C_1-C_4)$-alkyl;

$R^2$ is $(C_1-C_6)$-alkyl;

$R^3$ is $(C_1-C_6)$-alkyl, where the alkyl radical is optionally substituted by one or more fluorine atoms, $(C_2-C_6)$-alkenyl, $(C_2-C_6)$-alkynyl, $(C_3-C_7)$-cycloalkyl-$C_uH_{2u}$— or Het-$C_vH_{2v}$—, where u and v are selected from the group consisting of 1 and 2, or $R^3$ is a radical of a saturated or unsaturated 3-membered to 10-membered monocyclic or bicyclic ring which contains 0, 1, 2, 3 or 4 identical or different ring heteroatoms selected from the group consisting of N, O and S, where one or two of the ring nitrogen atoms may carry a hydrogen atom or a $(C_1-C_4)$-alkyl substituent and one or two of the ring sulfur atoms may carry one or two oxo groups and where the radical of a ring is optionally substituted at one or more ring carbon atoms by identical or different substituents $R^{31}$;

$R^5$ is halogen, hydroxyl, $(C_1-C_4)$-alkyl-, $(C_3-C_5)$-cycloalkyl-$C_zH_{2z}$—, $(C_1-C_4)$-alkyloxy, $(C_1-C_4)$-alkyl-$S(O)_m$—, amino, nitro, cyano, hydroxycarbonyl, $(C_1-C_4)$-alkyloxycarbonyl, aminocarbonyl or aminosulfonyl, where z is selected from the group consisting of 0, 1 and 2;

$R^{31}$ is halogen, $(C_1-C_4)$-alkyl, $(C_3-C_7)$-cycloalkyl, hydroxyl, $(C_1-C_4)$-alkyloxy, oxo, $(C_1-C_4)$-alkyl-$S(O)_m$—, amino, $(C_1-C_4)$-alkylamino, di($(C_1-C_4)$-alkyl)amino, $(C_1-C_4)$-alkylcarbonylamino, $(C_1-C_4)$-alkylsulfonylamino, nitro, cyano, $(C_1-C_4)$-alkylcarbonyl, aminosulfonyl, $(C_1-C_4)$-alkylaminosulfonyl or di($(C_1-C_4)$-alkyl)aminosulfonyl;

m is selected from the group consisting of 0, 1 and 2, where all numbers m are independent of one another.

A further embodiment relates to compounds of the formula I in which one or more radicals have the following meanings:

A is —$CH_2$— or O;

X is $(C_1-C_6)$-alkanediyloxy, where the oxygen atom of the $(C_1-C_6)$-alkanediyloxy group is attached to the group Y;

Y is phenylene, where the phenylene is optionally substituted at one or more ring carbon atoms by identical or different substituents $R^5$;

$R^1$ is hydrogen or $(C_1-C_4)$-alkyl;

$R^2$ is $(C_1-C_6)$-alkyl;

$R^3$ is $(C_1-C_6)$-alkyl, where the alkyl radical is optionally substituted by one or more fluorine atoms, or phenyl, where the phenyl radical is optionally substituted at one or more ring carbon atoms by identical or different substituents $R^{31}$;

$R^5$ is halogen, hydroxyl, $(C_1-C_4)$-alkyl-, $(C_3-C_5)$-cycloalkyl-$C_zH_{2z}$—, $(C_1-C_4)$-alkyloxy, $(C_1-C_4)$-alkyl-$S(O)_m$—, amino, nitro, cyano, hydroxycarbonyl, $(C_1-C_4)$-alkyloxycarbonyl, aminocarbonyl or aminosulfonyl, where z is selected from the group consisting of 0, 1 and 2;

$R^{31}$ is halogen, $(C_1-C_4)$-alkyl, $(C_3-C_7)$-cycloalkyl, hydroxyl, $(C_1-C_4)$-alkyloxy, oxo, $(C_1-C_4)$-alkyl-$S(O)_m$—, amino, $(C_1-C_4)$-alkylamino, di($(C_1-C_4)$-alkyl)amino, $(C_1-C_4)$-alkylcarbonylamino, $(C_1-C_4)$-alkylsulfonylamino, nitro, cyano, $(C_1-C_4)$-alkylcarbonyl, aminosulfonyl, $(C_1-C_4)$-alkylaminosulfonyl or di($(C_1-C_4)$-alkyl)aminosulfonyl;

m is selected from the group consisting of 0, 1 and 2.

A further embodiment relates to compounds of the formula I in which one or more radicals have the following meanings:

A is —$CH_2$— or O;

X is $(C_1-C_6)$-alkanediyloxy, where the oxygen atom of the $(C_1-C_6)$-alkanediyloxy group is attached to the group Y;

Y is phenylene, where the phenylene is optionally substituted at one or more ring carbon atoms by identical or different substituents $R^5$;

$R^1$ is hydrogen;

$R^2$ is $(C_1-C_6)$-alkyl;

$R^3$ is $(C_1-C_6)$-alkyl, where the alkyl radical is optionally substituted by one or more fluorine atoms, or phenyl, where the phenyl radical is optionally substituted at one or more ring carbon atoms by identical or different substituents $R^{31}$;

$R^5$ is $(C_1-C_4)$-alkyl;

$R^{31}$ is halogen.

Likewise, also with respect to all specific compounds disclosed herein, such as the example compounds which represent embodiments of the invention wherein the various groups and numbers in the general definition of the compounds of the formula I have the specific meanings present in the respective specific compound, it applies that they are a subject of the present invention in any of their stereoisomeric forms and/or a mixture of stereoisomeric forms in any ratio, and in the form of their physiologically acceptable salts, and in the form of the physiologically acceptable solvates of any of them. Irrespective of whether a specific compound is disclosed herein as a free compound and/or as a specific salt, the invention provides the compound both in the form of the free compound and in the form of all its physiologically acceptable salts, and if a specific salt is disclosed, additionally in the form of this specific salt, and in the form of the physiologically acceptable solvates of any of them. Thus, the invention also provides a compound of the formula I which is chosen from any one or more of the specific compounds of the formula I disclosed herein, including the example compounds specified below, and the physiologically acceptable salts thereof, and the physiologically acceptable solvates of any of them, wherein the invention provides the compound of the formula I in any of its stereoisomeric forms or as a mixture of stereoisomeric forms in any ratio, if applicable. Mentioned as an example is a compound of the formula I, or a physiologically acceptable solvate thereof, which is chosen from {4-[7-isobutyl-5-(3,3,3-trifluoropropoxy)oxazolo[5,4-d]pyrimidin-2-yl]-2,6-dimethylphenoxy}acetic acid, {4-[5-(3-chlorophenoxy)-7-isobutyloxazolo[5,4-d]pyrimidin-2-yl]-2,6-dimethylphenoxy}acetic acid, {4-[5-(3-chlorophenoxy)-7-propyloxazolo[5,4-d]pyrimidin-2-yl]-2,6-dimethylphenoxy}acetic acid, {4-[(5-(4-chlorobenzyl)-7-isobutyloxazolo[5,4-d]pyrimidin-2-yl]-2,6-dimethylphenoxy}acetic acid, [4-(5-benzyl-7-isobutyloxazolo[5,4-d]pyrimidin-2-yl)-2,6-dimethylphenoxy]acetic acid and {4-[5-(4-chlorobenzyl)-7-isopropyloxazolo[5,4-d]pyrimidin-2-yl]-2,6-dimethylphenoxy}acetic acid.

Another subject of the present invention are processes for the preparation of the compounds of the formula I and their salts and solvates, by which the compounds are obtainable and which are outlined in the following. In one process, a compound of the formula II is reacted with a compound of the formula III to give a compound of the formula I

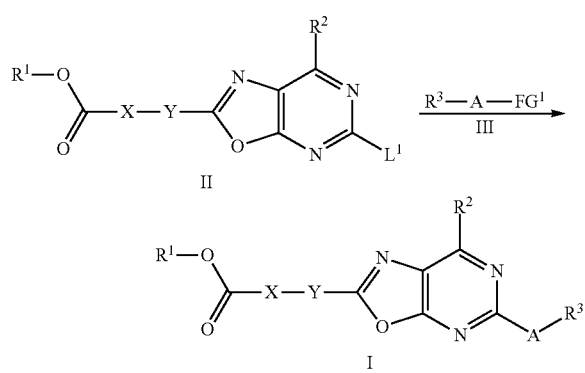

where the groups A, X, Y, $R^1$, $R^2$ and $R^3$ in the compounds of the formulae II and III are defined as in the compounds of the formula I and additionally functional groups can be present in protected form or in the form of a precursor group which is later converted into the final group. The group $L^1$ in the compounds of the formula II is a leaving group which can be replaced in an optionally catalyzed aromatic substitution reaction, such as a halogen atom, for example fluorine, chlorine, bromine or iodine, or an alkylthio or sulfoxide group or a sulfone group, for example a group of the formula —S-Alk- or —S(O)-Alk or —S(O)$_2$-Alk where Alk is a ($C^1$-$C^4$)-alkyl group, for example methyl or ethyl. The group $FG^1$ in the compounds of the formula III is a group which can be cleaved off in an optionally catalyzed aromatic substitution reaction from the reagent of the formula III and does not remain in the product of the formula I. Thus, $FG^1$ may, for example, be a proton, in particular for compounds of the formula III in which A is NH, O or S. Alternatively, $FG^1$ can be a boronic acid or boronic ester radical, a trialkylstannyl radical or a lithium, zinc halide or magnesium halide radical, in particular for compounds of the formula III in which A is a bond or —CH$_2$—.

The reaction of the compounds of the formulae II and III is an optionally catalyzed aromatic substitution reaction at the carbon atom in position 6 of the oxazolo[5,4-d]pyrimidine ring, i.e. in the pyrimidine grouping, and can be carried out under standard conditions for such reactions, which are well known to the person skilled in the art. The reaction can also be carried out in the presence of catalyst systems, for example sodium tolylsulfinate or iron, copper or palladium salts or complexes. In general, the reaction is carried out in an inert solvent, for example a hydrocarbon such as benzene, toluene, xylene or chlorobenzene, an ether such as tetrahydrofuran (THF), dioxane, dibutyl ether, diisopropyl ether or 1,2-dimethoxyethane (DME), an amine such as N,N-dimethylformamide (DMF), N,N-dimethylacetamide (DMA) or N-methylpyrrolidin-2-one (NMP) or a solvent mixture, at temperatures of from about −20° C. to about 250° C., for example at temperatures of from about 40° C. to about 200° C., depending on the particular circumstances of the case in question. In general, it is favorable to add a base to increase the reactivity, for example a tertiary amine, such as triethylamine, ethyldiisopropylamine or N-methylmorpholine, or an inorganic base such as an alkaline earth metal hydride, hydroxide, carbonate or bicarbonate such as sodium hydride, sodium hydroxide, potassium hydroxide, sodium carbonate, potassium carbonate, cesium carbonate or sodium bicarbonate or an alkoxide or amide such as sodium methoxide, sodium ethoxide, potassium methoxide, potassium tert-butoxide, sodium amide or lithium diisopropylamide. Prior to the reaction with the compound of the formula II, a compound of the formula III in which $FG^1$ is a proton may also separately be treated with a base and converted into a salt. If the reaction is carried out in the presence of a catalyst system, it is possible to employ catalysts which may comprise a metal ion or a metal in oxidation state 0; preference is given to using iron, copper or palladium. The catalysis frequently requires the presence of certain metal-complexing ligands which enable the formation of a catalytically active species in the first place or stabilize it. Metal/ligand complexes may be added to the reaction or be formed in situ. Such catalyst systems may comprise, for example, copper or copper(I) salts, especially copper(I) halides or copper(I) carboxylates, in particular copper(I) iodide or copper(I) thiophenecarboxylate, or else preformed copper(I) complexes, for example tetrakis(acetonitrile)copper(I) hexafluorophoshate, alone or in the presence of ligands, for example diamine ligands or 1,10-phenanthroline. Furthermore, such catalyst systems may consist of or be formed by, for example, palladium complexes or palladium salts in the presence of ligands, for example from palladium (0) complexes, in particular tris(dibenzylideneacetone)dipalladium(0), or palladium acetate, palladium trifluoroacetate or palladium halides, in particular palladium chloride, in the presence of ligands, in particular diphosphine ligands such as, for example, 2,2'-bis(diphenylphosphino)-1-1'-binaphthyl or 4,5-bis(diphenylphosphino)-9,9-dimethylxanthene or preformed complexes such as bis(tri-tert-butylphosphine)palladium(0). Furthermore, such catalyst systems may also comprise iron(III) salts such as, for example, iron(III) acetylacetonate. It is also possible to use simple catalysts; a nucleophilic aromatic substitution of 2-pyrimidine halides, in particular chlorides, by substituted alkali metal or alkaline earth metal benzenesulfinate, for example, can be catalyzed in particular by sodium tolylsulfinate.

The starting materials of the formulae II and III can be obtained by processes described in the literature or analogously to processes described in the literature, and in many cases they are commercially available. Compounds of the formula IIa, i.e compounds of the formula II in which $L^1$ is, for example, a sulfoxide group of the formula Alk-S(O)— or a sulfone group of the formula Alk-S(O)$_2$—, can be obtained by reacting an aminomalonic ester of the formula IV with an activated carboxylic acid derivative of the formula V to give a compound of the formula VI, reacting the latter compound with thiourea of the formula VII to give a compound of the formula VIII, alkylating the thiol with an alkylation reagent of the formula IX to give the thioether of the formula X, cyclizing the latter compound with formation of the oxazolo[5,4-d]pyrimidine ring system to give the compound of the formula XI, converting the latter compound into a compound of the formula XII into which the radical $R^1$O—C(O)—X— is introduced by reaction with a compound of the formula XIII to give the compound of the formula XIV, subsequently reacting the compound of the formula XIV with a compound of the formula XV to give a compound of the formula XVI and oxidizing the thioether grouping in the resulting compound of the formula XVI to give the corresponding sulfoxide or sulfone of the formula IIa.

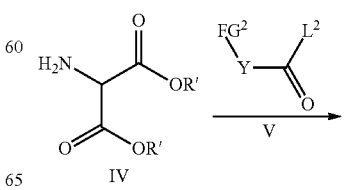

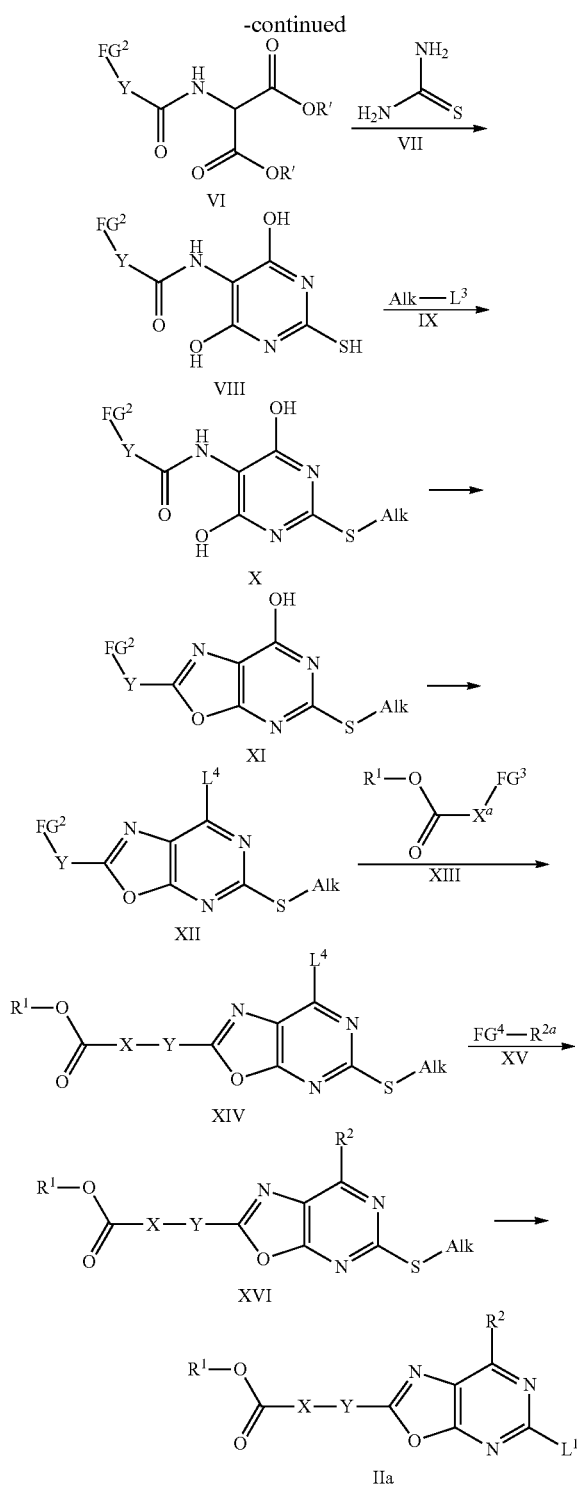

The group $X^a$ in the compounds of the formula XIII is defined like the group X in the compounds of the formula I or comprises a part of the group X in the desired compound of the formula II, such that after the reaction of the compounds of the formulae XII and XIII the group $X^a$ and any parts of the groups $FG^2$ and $FG^3$ remaining in the compound of the formula XIV together form the desired group X. Thus, for example, in the case that group X is an alkanediyloxy group, the group $X^a$ in the compound of the formula XIII may be the desired alkanediyloxy group and the group $FG^3$ may be a hydrogen atom attached to the oxygen atom, or the group $X^a$ may be the alkanediyl moiety, the group $FG^3$ is a leaving group and the group $FG^2$ in the compound of the formula XII is a hydroxyl group whose oxygen atom together with the alkanediyl moiety then, after the alkylation of the compound of the formula XII with the compound of the formula XIII, forms the desired alkanediyloxy group.

The groups $FG^2$ and $FG^3$ in the compounds of the formulae V, VI, VIII, X, XI, XII and XIII are functional groups which are suitable for the type of coupling used for the formation of the desired group X from the group $X^a$ and any part of groups $FG^2$ and $FG^3$ remaining in the compound of the formula XIV. If, for example, the group $X^a$ is attached via a nucleophilic substitution reaction to the group $Y^2$ or to an atom in the group $FG^2$, like an oxygen atom in a hydroxyl group representing $FG^2$, as mentioned above, $FG^3$ may be a leaving group such as a halogen atom such as chlorine, bromine or iodine, or a sulfonyloxy group such as methanesulfonyloxy, trifluoromethanesulfonyloxy or toluenesulfonyloxy. If the group $X^a$ is attached via a transition metal-catalyzed reaction to the group Y, $FG^3$ may be a leaving group such as a boronic acid, boronic ester, dialkylborane or trialylstannyl group, and in this case $FG^2$ may be halogen. $FG^3$ may also be a hydrogen atom or a carbon atom which is part of a double bond in an alkenediyl group representing $X^a$, if a Heck reaction is employed to link $X^a$ with Y, and in this case $FG^2$ may be halogen. When a Wittig reaction or a Wittig-Horner reaction is employed to link $X^a$ to Y, $FG^3$ may be a phosphonio group such as triphenylphosphonio or a phosphonyl group such as diethylphosphonyl, and the compound of the formula XIII may be a phosphonium salt or a phosphonic ester, and in this case $FG^2$ may be an aldehyde group —C(O)—H or a ketone group —C(O)-alkyl, and vice versa. In general, the group $FG^2$ is located at the carbon atom in the phenylene group or heterocyclic group which represents Y, which, in the compounds of the formulae XIV, XVI, IIa and I, carries the group X. The group $FG^2$ in the compounds of the formulae V, VI, VIII, X, XI and XII may also be present in protected form or in the form of a precursor group which is at a later point converted into the group which in the compound of the formula XII reacts with the compound of the formula XIII. Thus, for example, a hydroxyl groupp which represents $FG^2$ in the compound of the formula XII may be present in protected form in the compounds of the formulae V, VI, VIII, X and XI, for example in the form of an etherified hydroxyl group such as a benzyl ether or an alkyl ether such as a methyl ether. Such ethers can be cleaved using methods which are well-known to the person skilled in the art. A summary of methods to remove protective groups can be found in the literature, for example in P. J. Kocienski, Protecting Groups (Thieme Verlag, 1994), or T. W. Greene and P. G. M. Wuts, Protective Groups in Organic Synthesis (John Wiley & Sons, 1999).

The group $FG^4$ in the compound of the formula XV is a functional group suitable for coupling the compounds XIV and XV to give a compound of the formula XVI. Thus, $FG^4$ can be a lithium, zinc halide or magnesium halide radical if the compound of the formula XVI is formed via an optionally The groups X, Y, $R^1$ and $R^2$ in the compounds of the formulae IIa, V, VI, VIII, X, XI, XII, XIII, XIV and XVI are defined as in the compounds of the formula I, and additionally functional groups can be present in protected form or in the form of a precursor group which is later converted into the final group.

The group $R^{2a}$ in the compound of the formula XV is defined like the group $R^2$ in the compound of the formula I, but may additionally contain a double or triple bond adjacent to the bond to $FG^4$.

catalyzed nucleophilic aromatic substitution, or $FG^4$ can be a leaving group such as a boronic acid, boronic ester, dialkylborane or trialkylstannyl group if the formation of the compound of the formula XVI is a Suzuki- or Stille-type of coupling, or $FG^4$ may be a proton if $R^{2a}$ contains a double or triple bond adjacent to the bond to $FG^4$ and the compound XVI is formed via a Heck- or Sonogashira-type coupling reaction with subsequent hydrogenation.

The group $L^1$ in the compounds of the formula IIa is as defined above.

The group $L^2$ in the compounds of the formula V is a nucleophilically substitutable leaving group and may in particular be a halogen atom, such as chlorine or bromine, and the compound of the formula V may thus be a carbonyl halide. $L^2$ may also be a group of the formula $FG^2$-Y—C(O)—O, and the compound of the formula V may thus be a carboxylic anhydride, for example.

The group $L^3$ in compounds of the formula IX is a leaving group which can be replaced in a nucleophilic substitution reaction and may be in particular a halogen atom such as chlorine, bromine or iodine, or a sulfonyloxy group such as methanesulfonyloxy, trifluoromethanesulfonyloxy or toluenesulfonyloxy, i.e. the compound of the formula IX may be an organic halide or sulfonate, for example.

The group $L^4$ in compounds of the formulae XII and XIV is a leaving group which can be replaced in an aromatic substitution reaction and may be in particular a halogen atom such as chlorine, bromine or iodine.

The group R' in the compounds of the formulae IV and VI may be alkyl such as, for example, $(C_1-C_3)$-alkyl, such as methyl or ethyl.

As mentioned, the compounds of the formula XI may also be present in another tautomeric form, for example in the form of the respective 6H-oxazolo[5,4-d]pyrimidin-7-ones or 4H-oxazolo[5,4-d]pyrimidin-7-ones. If applicable, it applies to all compounds involved in the preparation of the compounds of the formula I that they may be present in a tautomeric form different from that shown in their formulae. In the reactions of this process for preparing the compounds of the formula II, as in all other reactions carried out in the preparation of the compounds of the formula I, starting materials may also be employed in the form of a salt and/or products may be obtained in the form of a salt. Thus, for example, compounds of the formula IV may be employed in the form of an acid addition salt such as the hydrochloride.

The reaction of the compounds of the formulae IV and V can be carried out under standard conditions for the acylation of an amine with an activated carboxylic acid derivative such as an acid halide or anhydride. In general, the reaction is carried out in an inert solvent, for example a hydrocarbon or a chlorinated hydrocarbon such as benzene, toluene, xylene, chlorobenzene, dichloromethane, chloroform or dichloroethane, an ether such as THF, dioxane, dibutyl ether, diisopropyl ether or DME, a ketone such as acetone or butan-2-one, an ester such as ethyl acetate or butyl acetate, or water, or a mixture of solvents, at temperatures of from about −10° C. to about 40° C., for example at temperatures of from about 0° C. to about 30° C. In general, the reaction is carried out with addition of a base, for example a tertiary amine, such as triethylamine, ethyldiisopropylamine or N-methylmorpholine or an inorganic base such as an alkali metal hydroxide, carbonate or bicarbonate such as sodium hydroxide, potassium hydroxide, sodium carbonate, potassium carbonate or sodium bicarbonate.

The reaction of the compounds of the formulae VI and VII is generally carried out in an inert solvent, for example an alcohol such as methanol, ethanol or isopropanol, or an ether such as THF, dioxane or DME, or a mixture of solvents, at temperatures of from about 20° C. to about 80° C., for example temperatures of about 40° C. to about 80° C., in the presence of a base, for example an alkoxide such as sodium methoxide, sodium ethoxide, potassium methoxide or potassium tert-butoxide.

The reaction of the compounds of the formulae VIII and IX is a nucleophilic substitution reaction at the carbon atom in the group Alk, which carries the group $L^3$, and can be carried out under standard conditions for such reactions, which are well-known to the person skilled in the art. In general, the reaction is, depending on the particular circumstances of the case in question, carried out in an inert solvent, for example a hydrocarbon or a chlorinated hydrocarbon such as benzene, toluene, xylene, chlorobenzene, dichloromethane, chloroform or dichloroethane, an ether such as THF, dioxane, dibutyl ether, diisopropyl ether or DME, an alcohol such as methanol, ethanol or isopropanol, a ketone such as acetone or butan-2-one, an ester such as ethyl acetate or butyl acetate, a nitrile such as acetonitrile, an amide such as DMF or NMP, or a mixture of solvents including two-phase mixtures with aqueous solutions, at temperatures of from about −20° C. to about 100° C., for example at temperatures of from about −10° C. to about 30° C. In general, it is favorable to add a base to increase the nucleophilicity of the compound of the formula VIII and/or to bind an acid released during the reaction, for example a tertiary amine, such as triethylamine, ethyldiisopropylamine or N-methylmorpholine, or an inorganic base such as an alkali metal hydride, hydroxide, carbonate or bicarbonate such as sodium hydride, sodium hydroxide, potassium hydroxide, sodium carbonate, potassium carbonate, cesium carbonate or sodium bicarbonate or an alkoxide or amide such as sodium methoxide, sodium ethoxide, potassium methoxide, potassium tert-butoxide, sodium amide or lithium diisopropylamide. Prior to the reaction with the compound of the formula IX, a compound of the formula VIII may also separately be treated with a base and converted into a salt.

The cyclization of the compound of the formula X to the compound of the formula XI can favorably be carried out in the presence of a phosphorus halide such as phosphorus pentachloride or phosphorus oxychloride or a mixture thereof, in an inert solvent, for example a hydrocarbon or a chlorinated hydrocarbon such as benzene, toluene, xylene, chlorbenzene, dichloromethane, chloroform or dichloromethane, at temperatures of from about 20° C. to about 100° C., for example at temperatures of from about 50° C. to about 80° C.

The conversion of the compound of the formula XI into a compound of the formula XII can likewise be carried out in the presence of a phosphorus halide such as phosphorus pentachloride or phosphorus oxychloride or a mixture thereof, in an inert solvent, for example a hydrocarbon or a chlorinated hydrocarbon such as benzene, toluene, xylene, chlorbenzene, dichloromethane, chloroform or dichloromethane, at temperatures of from about 20° C. to about 150° C., for example at temperatures of from about 50° C. to about 100° C. The compound of the formula X can also be converted directly, without isolation of the compound of the formula XI, into the compound of the formula XII.

The coupling of compounds of the formula XII with compounds of the formula XIII can be carried out using reactions of various types, as already mentioned above, for example via an alkylation reaction. Thus, the group Y can, for example when it carries a hydroxyl group which represents $FG^2$, be alkylated using a compound of the formula XIII in which $FG^3$ is a leaving group suitable for nucleophilic substitution reactions such as a halogen atom such as chlorine, bromine or iodine, or a sulfonyloxy group such as methanesulfonyloxy or toluenesulfonyloxy. The nucleophilic substitution reaction at the carbon atom of the group XIII which carries the group $FG^3$ can be carried out under standard conditions for such reactions, which are well-known to the person skilled in the art. In general, the reaction is, depending on the particular circumstances of the case in question, carried out in an inert solvent, for example a hydrocarbon or a chlorinated hydrocarbon such as benzene, toluene, xylene, chlorobenzene, dichloromethane, chloroform or dichloroethane, an ether such as THF, dioxane, dibutyl ether, diisopropyl ether or DME, an alcohol such as methanol, ethanol or isopropanol, a ketone such as acetone or butan-2-one, an ester such as ethyl acetate or butyl acetate, a nitrile such as acetonitrile, an amide such as N,N-dimethylformamide or N-methylpyrrolidin-2-one, or a mixture of solvents, at temperatures of from about 20° C. to about 100° C., for example at temperatures of from about 40° C. to about 80° C. In general, it is favorable to add a base to increase the nucleophilicity of the compound of the formula XIII and/or to bind an acid released during the reaction, for example a tertiary amine, such as triethylamine, ethyldiisopropylamine or N-methylmorpholine, or an inorganic base such as an alkali metal hydride, hydroxide, carbonate or bicarbonate such as sodium hydride, sodium hydroxide, potassium hydroxide, sodium carbonate, potassium carbonate, cesium carbonate or sodium bicarbonate or an alkoxide or amide such as sodium methoxide, sodium ethoxide, potassium methoxide, potassium tert-butoxide, sodium amide or lithium diisopropylamide. Prior to the reaction with the compound of the formula XIII, a compound of the formula XII in which $FG^2$ is hydroxyl may also separately be treated with a base and converted into a salt. A compound of the formula XII in which $FG^2$ is hydroxyl can be converted into a compound of the formula XIV not only by reaction with a compound of the formula XIII in which $FG^3$ is a leaving group, as indicated, but also by reaction with the corresponding alcohol, i.e. with a compound of the formula XIII in which $FG^3$ is hydroxyl, under the conditions, known to the person skilled in the art, of the Mitsunobu reaction. The coupling of compounds of the formula XII with compounds of the formula XIII via a transition metal-catalyzed reaction can also be carried out under the conditions of palladium-catalyzed crosscoupling reactions such as the Heck, Stille or Suzuki coupling reaction (see A. de Meijere and F. Diederich (Ed.), Metal-Catalyzed Cross-Coupling Reactions (Wiley-VCH, 2004)).

The reaction of compounds of the formula XIV with compounds of the formula XV to give compounds of the formula XVI can be carried out using reactions of various types, as already mentioned above, for example via an optionally catalyzed aromatic substitution reaction in which $FG^4$ may be a lithium, zinc halide or magnesium halide radical. In general, the reaction is carried out in an inert solvent, for example a hydrocarbon such as benzene, toluene, xylene or chlorobenzene, an ether such as tetrahydrofuran (THF), dioxane, dibutyl ether, diisopropyl ether or 1,2-dimethoxyethane (DME), an amine such as N,N-dimethylformamide (DMF), N,N-dimethylacetamide (DMA) or N-methylpyrrolidin-2-one (NMP) or a solvent mixture, at temperatures of from about 20° C. to about 250° C., for example at temperatures of from about 40° C. to about 200° C., depending on the particular circumstances of the case in question. The reaction can be carried out without catalysis or in the presence of a catalyst system; here, it is possible to employ catalysts which may comprise a metal ion or a metal in oxidation state 0; preference is given to using iron or palladium. The catalysis frequently requires the presence of certain metal-complexing ligands which enable the formation of a catalytically active species in the first place or stabilize it. Metal/ligand complexes may be added to the reaction or be formed in situ. For example, such catalyst systems may consist of or be formed by palladium complexes or palladium salts in the presence of ligands, for example from palladium(0) complexes, in particular tris(dibenzylideneacetone)dipalladium(0), or palladium acetate, palladium trifluoroacetate or palladium halides, in particular palladium chloride, in the presence of ligands, in particular diphosphine ligands such as, for example, 2,2'-bis(diphenylphosphino)-1-1'-binaphthyl or 4,5-bis(diphenylphosphino)-9,9-dimethylxanthene or pre-formed complexes such as bis(tri-tert-butylphosphine)palladium(0). Furthermore, such catalyst systems may also comprise iron(III) salts such as, for example, iron(III) acetylacetonate. Furthermore, the reaction of compounds of the formula XIV with compounds of the formula XV to give compounds of the formula XVI can be carried out via a Suzuki- or Stille-type coupling reaction, in which case $FG^4$ is a leaving group such as a boronic acid, boronic ester, dialkylborane or trialkylstannyl group. Furthermore, the reaction of compounds of the formula XIV with compounds of the formula XV to give compounds of the formula XVI can be carried out via a Heck- or Sonogashira-type coupling reaction, in which case $FG^4$ is a proton and $R^{2a}$ contains a double or triple bond adjacent to the bond to $FG^4$ and the double bond or triple bond resulting after the coupling reaction can be hydrogenated immediately or at a later stage under standard conditions known to the person skilled in the art in the presence of a catalyst such as, for example, palladium on activated carbon in a suitable inert solvent such as, for example, ethanol or ethyl acetate, leading back to compounds having a saturated radical $R^2$. These Suzuki-, Stille-, Heck- and Sonogashira-type coupling reactions can be carried out, for example, under palladium catalysis or under conditions as described in the literature (see A. de Meijere and F. Diederich (Ed.), Metal-Catalyzed Cross-Coupling Reactions (Wiley-VCH, 2004)).

The oxidation of the Alk-S group in the compounds of the formula XVI to the sulfoxide group or sulfone group in the compounds of the formula IIa can be carried out with the aid of hydrogen peroxide or a peracid such as 3-chloroperbenzoic acid or monoperoxyphthalic acid in an inert solvent, for example a chlorinated hydrocarbon such as dichloromethane or chloroform or an ester such as ethyl acetate or butyl acetate, at temperatures of from about 0° C. to about 40° C., for example at about 20° C.

The order of the steps in the preparation of the compounds of the formula I can also be changed.

Thus, for example, an aminomalonic ester of the formula IV such as the diethyl ester may initially be reacted with thiourea in the presence of an alkali metal alkoxide such as sodium ethoxide, the sulfur atom can then be alkylated, for example methylated with iodomethane, and the resulting product can be acylated with a compound of the formula V, thus giving a compound of the formula X.

Furthermore, for example, a compound of the formula XII can be reacted with a compound of the formula XV to give a compound of the formula XVII, and by subsequent reaction of the latter with a compound of the formula XIII, giving a compound of the formula XVI, and oxidation of the thioether grouping in the resulting compound of the formula XVI it is possible to obtain the corresponding sulfoxide or sulfone of the formula IIa.

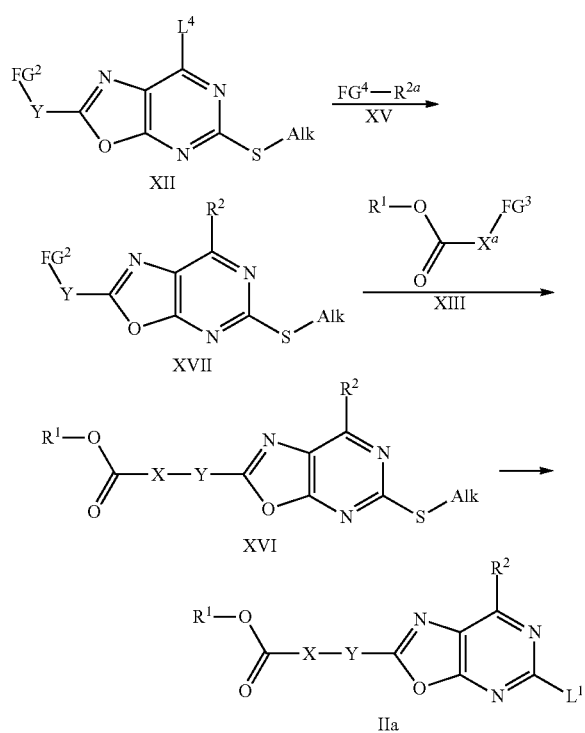

Here, the groups X, Y, $R^1$ and $R^2$ in the compounds of the formulae IIa, XII, XIII, XVI and XVII are as defined in the compounds of the formula I, and the groups $R^{2a}$, $X^a$, $L^1$, $L^4$, $FG^2$, $FG^3$ and $FG^4$ in the compounds of the formulae IIa, XII, XIII, XV and XVII are as defined above. The reactions can be carried out under the conditions described above.

In a further process for the synthesis of compounds of the formula I, a compound of the formula XVIII is reacted with a compound of the formula XV to give a compound of the formula I

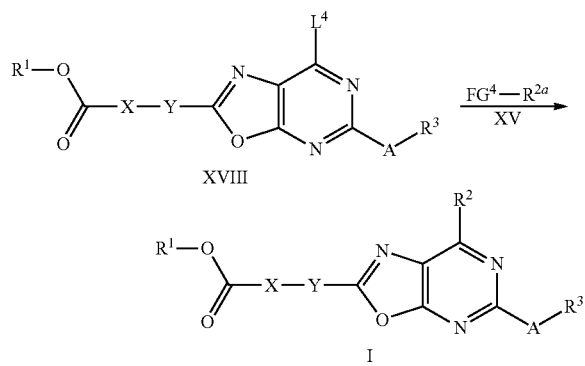

in which the groups A, X, Y, $R^1$, $R^2$ and $R^3$ in the compounds of the formula XVIII are as defined in the compounds of the formula I and in addition functional groups may be present in protected form or in the form of a precursor group which is converted into the final group at a later stage. The groups $L^4$, $FG^4$ and $R^{2a}$ in the compounds of the formulae XV and XVII are as defined above.

The reaction of compounds of the formula XVIII with compounds of the formula XV to give compounds of the formula I can be carried out using reactions of various types, as already mentioned above, for example via an optionally catalyzed aromatic substitution reaction in which $FG^4$ may be a lithium, zinc halide or magnesium halide radical. In general, the reaction is carried out in an inert solvent, for example a hydrocarbon such as benzene, toluene, xylene or chlorobenzene, an ether such as tetrahydrofuran (THF), dioxane, dibutyl ether, diisopropyl ether or 1,2-dimethoxyethane (DME), an amine such as N,N-dimethylformamide (DMF), N,N-dimethylacetamide (DMA) or N-methylpyrrolidin-2-one (NMP) or a solvent mixture, at temperatures of from about −20° C. to about 250° C., for example at temperatures of from about 0° C. to about 200° C., depending on the particular circumstances of the case in question. The reaction can be carried out without catalysis or in the presence of a catalyst system; here, it is possible to employ catalysts which may comprise a metal ion or a metal in oxidation state 0; preference is given to using iron or palladium. The catalysis frequently requires the presence of certain metal-complexing ligands which enable the formation of a catalytically active species in the first place or stabilize it. Metal/ligand complexes may be added to the reaction or be formed in situ. For example, such catalyst systems may consist of or be formed by palladium complexes or palladium salts in the presence of ligands, for example from palladium(0) complexes, in particular tris(dibenzylideneacetone)dipalladium(0), or palladium acetate, palladium trifluoroacetate or palladium halides, in particular palladium chloride, in the presence of ligands, in particular diphosphine ligands such as, for example, 2,2'-bis(diphenylphosphino)-1-1'-binaphthyl or 4,5-bis(diphenylphosphino)-9,9-dimethylxanthene or pre-formed complexes such as bis(tri-tert-butylphosphine)palladium(0). Furthermore, such catalyst systems may also comprise iron(III) salts such as, for example, iron(III) acetylacetonate. Furthermore, the reaction of compounds of the formula XVIII with compounds of the formula XV to give compounds of the formula I can be carried out via Suzuki- or Stifle-type coupling reactions, in which case $FG^4$ is a leaving group such as a boronic acid, boronic ester, dialkylborane or trialkylstannyl group. Furthermore, the conversion of compounds of the formula XVIII with compounds of the formula XV into compounds of the formula I can be carried out via Heck- or Sonogashira-type coupling reactions, in which case $FG^4$ is a proton and $R^{2a}$ contains a double or triple bond adjacent to the bond to $FG^4$ and the double bond or triple bond resulting after the coupling reaction can be hydrogenated immediately under standard conditions known to the person skilled in the art in the presence of a catalyst such as, for example, palladium on activated carbon in a suitable inert solvent such as, for example, ethanol or ethyl acetate, leading back to compounds having a saturated radical $R^2$. These Suzuki-, Stille-, Heck- and Sonogashira-type coupling reactions can be carried out, for example, under palladium catalysis or under conditions as described in the literature (see A. de Meijere and F. Diederich (Hrsg.), Metal-Catalyzed Cross-Coupling Reactions (Wiley-VCH, 2004)).

The starting materials of the formulae XV and XVIII can be obtained by processes described in the literature or analogously to processes described in the literature, and in many cases they are commercially available. Compounds of the formula XVIII can be obtained by reacting a compound of the formula XIV, which can be prepared as described above, by oxidizing the thioether grouping in the compound of the formula XIV to a sulfoxide or sulfone of the formula IXX and subsequent reaction of the latter with a compound of the formula III,

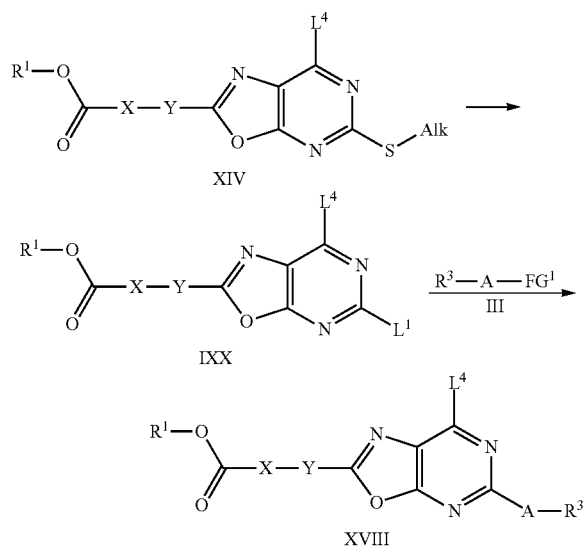

where the groups A, X, Y, $R^1$, $R^2$ and $R^3$ in the compounds of the formulae III, XIV, XVIII and IXX are defined as in the compounds of the formula I and additionally functional groups can be present in protected form or in the form of a precursor group which is later converted into the final group. The group $L^1$ in the compound IXX is as defined in the compound IIa and the groups $L^4$ and $FG^1$ in the compounds of the formulae III, XIV, XVIII and IXX are as defined above.

The oxidation of the Alk-S group in the compounds of the formula XIV to the sulfoxide group or sulfone group in the compounds of the formula IX can be carried out with the aid of hydrogen peroxide or a peracid such as 3-chloroperbenzoic acid or monoperoxyphthalic acid in an inert solvent, for example a chlorinated hydrocarbon such as dichloromethane or chloroform or an ester such as ethyl acetate or butyl acetate, at temperatures of from about 0° C. to about 40° C., for example at about 20° C.

The reaction of the compounds of the formulae IXX and III is an optionally catalyzed aromatic substitution reaction at the carbon atom in position 6 of the oxazolo[5,4-d]pyrimidine ring, i.e. in the pyrimidine grouping, and can be carried out under standard conditions for such reactions, which are well known to the person skilled in the art. The reaction can also be carried out in the presence of catalysts, for example substituted alkali metal or alkaline earth metal benzenesulfinates, in particular sodium tolylsulfinate. In general, the reaction is carried out in an inert solvent, for example a hydrocarbon such as benzene, toluene, xylene or chlorobenzene, an ether such as tetrahydrofuran (THF), dioxane, dibutyl ether, diisopropyl ether or 1,2-dimethoxyethane (DME), an amine such as N,N-dimethylformamide (DMF), N,N-dimethylacetamide (DMA) or N-methylpyrrolidin-2-one (NMP) or a solvent mixture, at temperatures of from about −80° C. to about 250° C., for example at temperatures of from about 0° C. to about 200° C., depending on the particular circumstances of the case in question. In general, it is favorable to add a base to increase the reactivity, for example a tertiary amine, such as triethylamine, ethyldiisopropylamine or N-methylmorpholine, or an inorganic base such as an alkaline earth metal hydride, hydroxide, carbonate or bicarbonate such as sodium hydride, sodium hydroxide, potassium hydroxide, sodium carbonate, potassium carbonate, cesium carbonate or sodium bicarbonate or an alkoxide or amide such as sodium methoxide, sodium ethoxide, potassium methoxide, potassium tert-butoxide, sodium amide or lithium diisopropylamide. Prior to the reaction with the compound of the formula II, a compound of the formula III in which $FG^1$ is a proton may also separately be treated with a base and converted into a salt. A reaction with compounds of the formula III in which $FG^1$ is a lithium halide, zinc halide or magnesium halide and A is a bond or —$CH_2$— can also be catalyzed by iron(III) salts such as, for example, iron(III) acetylacetonate.

Alternatively, it is also possible to react compounds of the formula XIV directly with compounds of the formula III to give compounds of the formula XVIII if $FG^1$ is a boronic acid or boronic ester radical or a trialkylstannyl and A is a bond or —$CH_2$—. This can be catalyzed by catalyst systems which comprise, for example, copper or copper(I) salts, especially copper(I) halides or copper(I) carboxylates, in particular copper(I) iodide or copper(I) thiophenecarboxylate, or else preformed copper(I) complexes, for example tetrakis(acetonitrile)copper(I) hexafluorophoshate, alone or in the presence of ligands, for example diamine ligands or 1,10-phenanthroline. In general, the reaction is carried out in an inert solvent, for example a hydrocarbon such as benzene, toluene, xylene or chlorobenzene, an ether such as tetrahydrofuran (THF), dioxane, dibutyl ether, diisopropyl ether or 1,2-dimethoxyethane (DME), an amine such as N,N-dimethylformamide (DMF), N,N-dimethylacetamide (DMA) or N-methylpyrrolidin-2-one (NMP) or a solvent mixture, at temperatures of from about 20° C. to about 250° C., for example at temperatures of from about 40° C. to about 200° C., depending on the particular circumstances of the case in question.

The order of the steps in the preparation of the compounds of the formula I can also be changed.

Thus, for example, initially a compound of the formula XII can be converted into a compound of the formula XX, this compound can then be reacted with a compound of the formula III to give a compound of the formula XXI, and the latter can then be reacted with a compound of the formula XIII giving a compound of the formula XVIII.

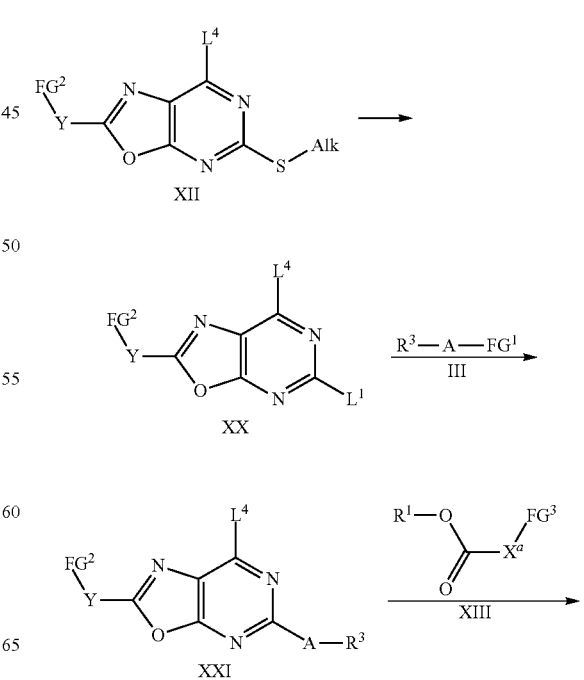

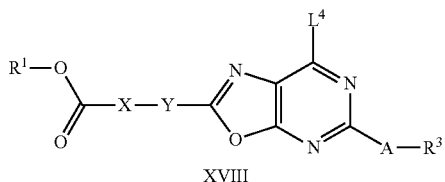

XVIII

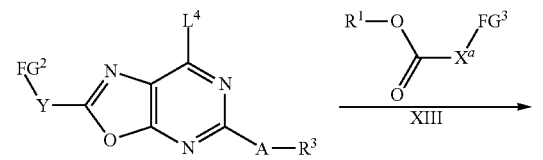

XXIa

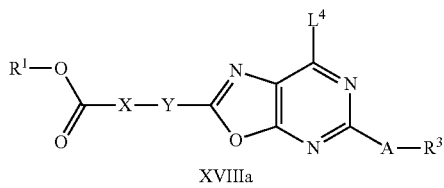

XVIIIa

Here, the groups A, X, Y, R¹ and R³ in the compounds of the formulae III, XII, XIII, XVIII, XX and XXI are as defined in the compounds of the formula I, the group L¹ in the compound of the formula XX is as defined in the compound IIa, and the groups $X^a$, $L^4$, $FG^1$, $FG^2$ and $FG^3$ in the compounds of the formulae III, XII, XIII, XVIII, XX and XXI are as defined above. The reactions can be carried out under the conditions described above. Alternatively, as described above, it is also possible to react compounds of the formula XII directly with compounds of the formula III to give compounds of the formula XXI if $FG^1$ is a boronic acid or boronic ester radical or a trialkylstannyl and A is a bond or —CH₂—.

Alternatively, compounds of the formula XVIIIa, i.e. compounds in which A is a bond or a CH₂ group can also be obtained by reacting an aminomalonic ester of the formula IV with an activated carboxylic acid derivative of the formula V to give a compound of the formula VI, reaction of the latter compound with an amidine of the formula XXIIa to give a compound of the formula XXIIIa, cyclization of the latter compound with formation of the oxazolo[5,4-d]pyrimidine ring system to give the compound of the formula XXIVa, conversion of the latter compound into a compound of the formula XXIa, and subsequent introduction of the radical R¹O—C(O)—X— by reaction with a compound of the formula XIII.

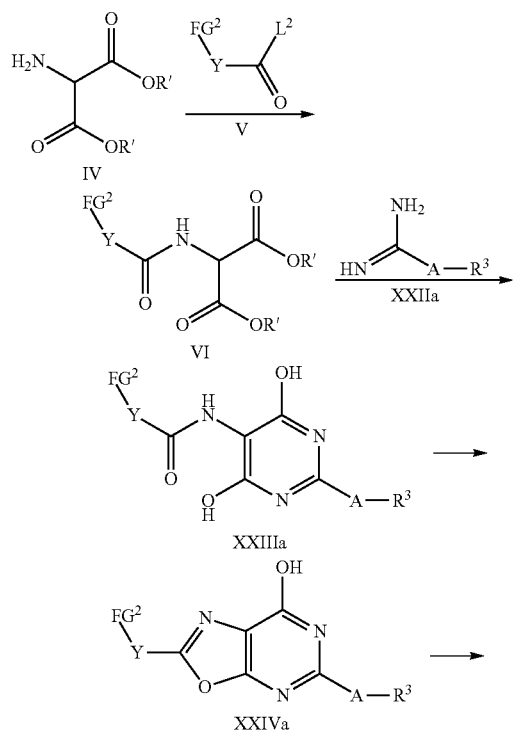

Here, the groups X, Y, R¹ and R³ in the compounds of the formulae V, VI, XIII, XVIIIa, XXIa, XXIIa, XXIIIa and XXIVa are as defined in the compounds of the formula I, the group A in the compounds of the formulae XVIIIa, XXIa, XXIIa, XXIIIa and XXIVa is a bond or a CH₂ group, and the meanings of the groups R', $X^a$, $L^2$, $L^4$, $FG^2$ and $FG^3$ in the compounds of the formulae IV, V, VI, XIII, XVIIIa, XXIa, XXIIa, XXIIIa and XXIVa are as defined above.

The conversion of the compounds IV and V into the compound VI is carried out as already described above. The reaction of the compounds of the formula VI with compounds of the formula XXIIa is generally carried out in an inert solvent, for example an alcohol such as methanol, ethanol or isopropanol, or an ether such as THF, dioxane or DME, or a mixture of solvents, at temperatures of from about 20° C. to about 200° C., for example temperatures of about 20° C. to about 100° C., in the presence of a base, for example an alkoxide such as sodium methoxide, sodium ethoxide, potassium methoxide or potassium tert-butoxide. Here, the amidine of the formula XXIIa can also be employed as a salt, for example as a hydrochloride. The cyclization of the compounds of the formula XXIIIa into compounds of the formula XXIVa and the conversion into the compounds of the formula XXIa can be carried out under conditions as described above for the conversion of the compounds of the formula X into compounds of the formula XI and the conversion of the compounds of the formula XI into the compounds of the formula XII. The reaction of the compounds of the formula XXIa with compounds of the formula XIII to give compounds of the formula XVIIIa can be carried out under conditions described above for the reaction of the compounds of the formula XII with compounds of the formula XIII to give compounds of the formula XIV.

In a further process for the synthesis of compounds of the formula I, a compound of the formula XXV is reacted with a compound of the formula XIII to give a compound of the formula I

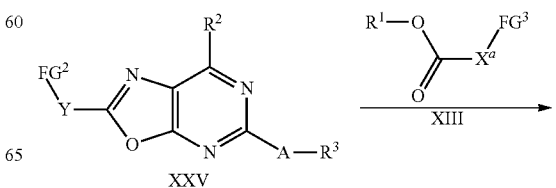

XXV

-continued

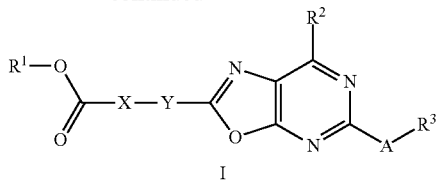

in which the groups A, X, Y, $R^1$, $R^2$ and $R^3$ in the compounds of the formulae XIII and XXV are defined as in the compounds of the formula I and additionally functional groups can be present in protected form or in the form of a precursor group which is later converted into the final group. The groups $X^a$, $FG^2$ and $FG^3$ in the compounds of the formulae XIII and XXV are as defined above.

Here, the conversion of compounds of the formula XXV into compounds of the formula I can be carried out under conditions already described above for the conversion of compounds of the formula XII into compounds of the formula XIV.

The starting materials of the formulae XXV and XIII can be obtained by processes described in the literature or analogously to processes described in the literature, and in many cases they are commercially available. Compounds of the formula XXV can be obtained by conversion of a compound of the formula XVII, which can be prepared as described above, into a compound of the formula XXVI and subsequent reaction of the latter with a compound of the formula III

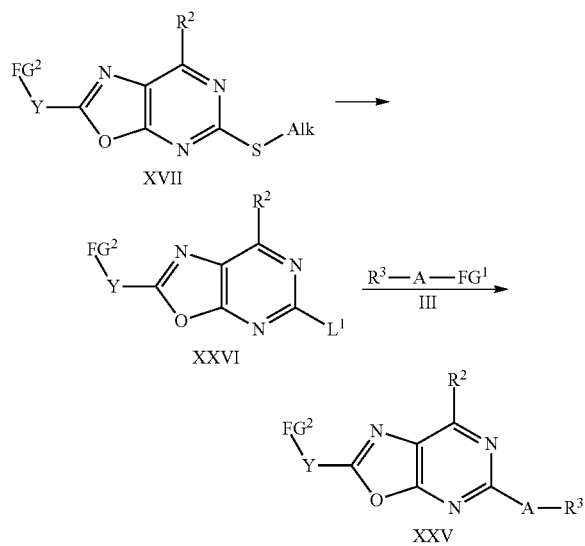

where the groups A, Y, $R^2$ and $R^3$ in the compounds of the formulae III, XVII, XXV and XXVI are defined as in the compounds of the formula I and additionally functional groups can be present in protected form or in the form of a precursor group which is later converted into the final group. The group $L^1$ in the compound XXVI is as defined in the compound IIa and the groups $FG^1$ and $FG^2$ in the compounds of the formulae III, XVII, XXV and XXVI are as defined above.

Here, the conversion of a compound of the formula XVII into a compound of the formula XXVI can be carried out under conditions already described above for the conversion of compounds of the formula XVI into compounds of the formula IIa. The reaction of compounds of the formula XXVI with compounds of the formula III to give compounds of the formula XXV can be carried out under conditions already described above for the conversion of compounds of the formula IIa into compounds of the formula I.

Furthermore, compounds of the formula XXV can be obtained by reacting a compound of the formula XXI, which can be prepared as described above, with a compound of the formula XV

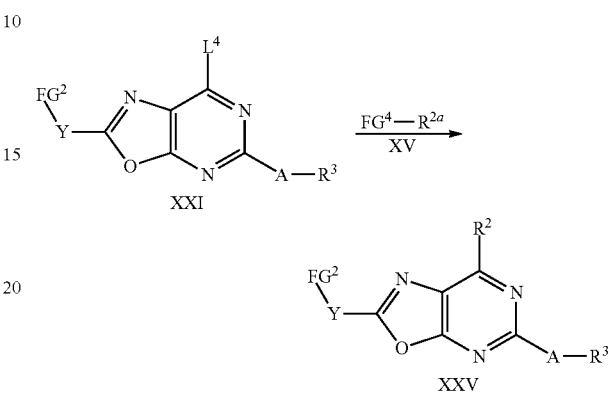

where the groups A, Y, $R^2$ and $R^3$ in the compounds of the formulae XXI and XXV are defined as in the compounds of the formula I and additionally functional groups can be present in protected form or in the form of a precursor group which is later converted into the final group. The groups $L^4$, $R^{2a}$, $FG^2$ and $FG^4$ in the compounds of the formulae XV, XXI and XXV are as defined above.

Here, the reaction of compounds of the formula XXI with compounds of the formula XV to give compounds of the formula XXV can be carried out under conditions already described above for the conversion of compounds of the formula XIV into compounds of the formula XIV.

Further compounds of the formula I can be obtained from suitable compounds prepared according to the above-described processes by functionalization or modification of any functional groups present according to standard procedures, for example by esterification, amidation, hydrolysis, etherification, alkylation, acylation, sulfonylation, reduction, oxidation, conversion into salts, and others. For example, a hydroxyl group, which may be liberated from an ether group by ether cleavage, for example by means of boron tribromide, or from a protected hydroxyl group by deprotection, can be esterified to give a carboxylic acid ester or a sulfonic acid ester, or etherified. Etherifications of hydroxyl groups can favorably be performed by alkylation with the respective halogen compound, for example a bromide or iodide, in the presence of a base, for example an alkaline metal carbonate such as potassium carbonate or cesium carbonate, in an inert solvent, for example an amide like DMF or NMP or a ketone like acetone or butan-2-one, or with the respective alcohol under the conditions of the Mitsunobu reaction referred to above. A hydroxyl group can be converted into a halide by treatment with a halogenating agent. A halogen atom can be replaced with a variety of groups in a substitution reaction which may also be a transition-metal catalyzed reaction. A nitro group can be reduced to an amino group, for example by catalytic hydrogenation. An amino group can be modified under standard conditions for alkylation, for example by reaction with a halogen compound or by reductive amination of a carbonyl compound, or for acylation or sulfonylation, for example by reaction with a reactive carboxylic acid derivative, like an acid chloride or anhydride or a sulfonic acid chloride, or with an activated carboxylic acid which may be obtained from the carboxylic acid by treatment with a coupling agent like N,N'-carbonyldiimidazole (CDI), a carbodiimide such as 1,3-dicyclohexylcarbodiimide (DCC) or 1-(3-dimethylaminopropyl)-3-ethylcarbodiimide hydrochloride (EDC), O-(7-azabenzotriazol-1-yl)-N,N,N',N'-tetramethyluronium hexafluorophosphate (HATU), O-(cyano(ethoxycarbonyl)methyleneamino)-N,N,N',N'-tetramethyluronium tetrafluoroborate (TOTU) or [(benzotriazol-1-yloxy) dimethylaminomethylene]dimethylammonium tetrafluoroborate (TBTU), for example. A carboxylic ester group can be hydrolyzed under acidic or basic conditions to give a carboxylic acid. A carboxylic acid group can be activated or converted into a reactive derivative as mentioned above and reacted with an alcohol or an amine or ammonia to give an ester or amide. A primary amide can be dehydrated to give a nitrile. A sulfur atom, for example in an alkyl-S group or in a heterocyclic ring, can be oxidized with a peroxide like hydrogen peroxide or a peracid to give a sulfoxide moiety $S(O)$ or a sulfone moiety $S(O)_2$. A carboxylic acid group, a carboxylic acid ester group and a ketone group can be reduced to an alcohol, for example by means of a complex hydride such as lithium aluminum hydride, lithium borohydride or sodium borohydride. A compound of the formula I or an intermediate such as a compound of the formula II, which contains a double bond or a triple bond in the group X, which can be readily obtained via a transition metal-catalyzed coupling reaction from a compound of the formula XIV containing a double or triple bond in the group $X^a$ and a compound of the formula XIII as outlined above, can be converted into a compound in which X is a saturated group, by hydrogenation in the presence of hydrogenation catalyst such as a palladium catalyst.

All reactions used in the above-described syntheses of the compounds of the formula I are per se well known to the skilled person and can be carried out under standard conditions according to, or analogously to, procedures described in the literature, for example in Houben-Weyl, Methoden der Organischen Chemie (Methods of Organic Chemistry), Thieme-Verlag, Stuttgart, or Organic Reactions, John Wiley & Sons, New York. If desired, the obtained compounds of the formula I, as well as any intermediate compounds, can be purified by customary purification procedures, for example by recrystallization or chromatography. As already mentioned, all starting compounds and intermediates employed in the above-described syntheses which contain an acidic or basic group, can also be employed in the form of salts, and all intermediates and final target compounds can also be obtained in the form of salts. As likewise mentioned above, depending on the circumstances of the specific case, in order to avoid an unwanted course of a reaction or side reactions during the synthesis of a compound it can generally be necessary or advantageous to temporarily block functional groups by introducing protective groups and deprotect them at a later stage of the synthesis, or to introduce functional groups in the form of precursor groups which later are converted into the desired functional groups. As examples of protecting groups amino-protecting groups may be mentioned which can be acyl groups or alkyloxycarbonyl groups, for example a tert-butyloxycarbonyl group (=Boc) which can be removed by treatment with trifluoroacetic acid (=TFA), a benzyloxycarbonyl group which can be removed by catalytic hydrogenation, or a fluoren-9-ylmethoxycarbonyl group which can be removed by treatment with piperidine, and protecting groups of carboxylic acid groups which can be protected as ester groups, such as tert-butyl esters which can be deprotected by treatment with trifluoroacetic acid, or benzyl esters which can be deprotected by catalytic hydrogenation. As an example of a precursor group the nitro group, which can be converted into an amino group by reduction, for example by catalytic hydrogenation, may be mentioned. Such synthesis strategies, and protective groups and precursor groups which are suitable in a specific case, are known to the skilled person.

Another subject of the present invention are the novel starting compounds and intermediates occurring in the synthesis of the compounds of the formula I, including the compounds of the formulae II, III, IV, V, VI, VII, VIII, IX, X, XI, XII, XIII, XIV, XV, XVI, XVII, XVIII, IXX, XX, XXI, XXII, XXIII, XXIV, XXV and XXVI in which Alk, A, X, $X^a$, $R^1$, $R^2$, $R^{2a}$, $R^3$, $FG^1$, $FG^2$, $FG^3$, $FG^4$, $L^1$, $L^2$, $L^3$ and $L^4$ are defined as above, in any of their stereoisomeric forms or a mixture of stereoisomeric forms in any ratio, and their salts, and solvates of any of them, and their use as intermediates. The invention also includes all tautomeric forms of the said intermediates and starting compounds. All explanations given above and embodiments specified above with respect to the compounds of the formula I also apply correspondingly to the said intermediates and starting materials. Subject of the invention are in particular the novel specific starting compounds and intermediates disclosed herein. Independently thereof whether they are disclosed as a free compound and/or as a specific salt, they are a subject of the invention both in the form of the free compounds and in the form of their salts, and if a specific salt is disclosed, additionally in the form of this specific salt, and in the form of solvates of any of them.

The compounds of the formula I, optionally in combination with other pharmacologically active compounds, can be administered to animals, in particular to mammals including humans, as pharmaceuticals by themselves, in mixtures with one another, or in the form of pharmaceutical compositions. The administration can be carried out orally, for example in the form of tablets, film-coated tablets, sugar-coated tablets, granules, hard and soft gelatin capsules, solutions including aqueous, alcoholic and oily solutions, juices, drops, syrups, emulsions or suspensions, rectally, for example in the form of suppositories, or parenterally, for example in the form of solutions for subcutaneous, intramuscular or intravenous injection or infusion, in particular aqueous solutions. The compounds of the formula I can additionally be used in modes of local drug delivery, for example in coated stents for preventing or reducing in-stent restenosis or by applying them locally by means of a catheter. The appropriate administration form depends, among others, on the disease to be treated and on its severity.

The compounds of the formula I can also be administered topically. Pharmaceutical compositions suitable for topical use on the skin are in the form of ointment, cream, lotion, paste, gel, hydrogel, spray, aerosol or oil. Carriers which can be used are petrolatum, lanolin, polyethylene glycols, alcohols and combinations of two or more of these substances. The active ingredient is generally present in a concentration of 0.0001 to 15% by weight of the composition, for example 0.0005 to 2%.

In one embodiment, the topical preparation is present as a gel.

In a further embodiment, the topical preparation is present as a hydrogel.

A hydrogel is understood as meaning a polymer which comprises, but is insoluble in, water, and whose molecules are linked chemically, for example by covalent or ionic bonds, or physically, for example by loop formation of the polymer chains, to form a three-dimensional network. Owing to incorporated hydrophilic polymer components, they swell in water with a considerable increase in volume, but without losing their material hold. A hydrogel consists, for example, of a hydrophilic solvent (for example water), a moisturizer (for example glycerol) and a gel former (for example croscarmellose-sodium).

The examples below show suitable gel preparations:

PREPARATION EXAMPLE 1

| Compound of example 1 | 0.0004% |
|---|---|
| Glycerol 85% | 10% |
| Methylparaben | 0.2% |
| Propylparaben | 0.03% |
| Croscarmellose-sodium | 4% |
| HCl/NaOH | qs (to adjust the pH to 7.5) |
| Water | ad 100% |

PREPARATION EXAMPLE 2

| Compound of example 1 | 0.04% |
|---|---|
| Glycerol 85% | 10% |
| Methylparaben | 0.2% |
| Propylparaben | 0.03% |
| Croscarmellose-sodium | 4% |
| HCl/NaOH | qs (to adjust the pH to 7.5) |
| Water | ad 100% |

PREPARATION EXAMPLE 3

| Compound of example 1 | 0.0004% |
|---|---|
| PEG400 | 10% |
| Methylparaben | 0.2% |
| Propylparaben | 0.03% |
| Croscarmellose-sodium | 4% |
| HCl/NaOH | qs (to adjust the pH to 7.5) |
| Water | ad 100% |

PREPARATION EXAMPLE 4

| Compound of example 1 | 0.04% |
|---|---|
| PEG400 | 10% |
| Methylparaben | 0.2% |
| Propylparaben | 0.03% |
| Croscarmellose-sodium | 4% |
| HCl/NaOH | qs (to adjust the pH to 7.5) |
| Water | ad 100% |

The hydrogels are preparations for dermal application. The hydrogels can be applied to open wound regions. The hydrogels comprise the medicament in dissolved form, thus ensuring rapid skin and tissue penetration.

An aseptic preparation process ensures that no additional microbiological contaminations enter the wound as a result of the application of the medicament. In one embodiment, preservatives (methyl- and propylparaben) are additionally incorporated into the hydrogel to keep the pathogen load low.

In one embodiment, the hydrogel comprises the compounds of the formula I in concentrations of 0.04-0.0004% (m/m).

The aseptic hydrogel is stored in suitable sterile containers. In one embodiment, the hydrogel is stored in sterile containers made of polypropylene.

The amount of a compound of the formula I and/or its physiologically acceptable salts and/or solvates present in the pharmaceutical compositions normally ranges from about 0.2 to about 800 mg, for example from about 0.5 to about 500 mg, for example from about 1 to about 200 mg, per unit dose, but depending on the type of the pharmaceutical composition it may also be higher. The pharmaceutical compositions usually comprise from about 0.5 to about 90 percent by weight of the compound of the formula I and/or its physiologically acceptable salts and/or solvates. The production of the pharmaceutical compositions can be carried out in a manner known per se. To this end, one or more compounds of the formula I and/or their physiologically acceptable salts and/or solvates together with one or more solid or liquid pharmaceutical carrier substances, or vehicles, and/or additives, or auxiliary substances, and, if a combination medicament is desired, other pharmacologically active compounds having therapeutic or prophylactic action are brought into a suitable form for administration and dosage which can be used in human or veterinary medicine. As carrier substances and additives, suitable organic and inorganic substances can be used which do not react in an undesired manner with the compounds of the formula I or their physiologically acceptable salts or solvates. As examples of types of additives which can be contained in the pharmaceutical compositions and medicaments, lubricants, preservatives, thickeners, stabilizers, disintegrants, wetting agents, agents for achieving a depot effect, emulsifiers, salts, for example for influencing the osmotic pressure, buffer substances, colorants, flavorings and aromatic substances may be mentioned. Examples of carrier substances and additives are water, physiological sodium chloride solution, vegetable oils, waxes, alcohols such as ethanol, isopropanol, 1,2-propanediol, benzyl alcohols or glycerol, polyols, mannitol, polyethylene glycols, polypropylene glycols, glycerol triacetate, polyvinylpyrrolidone, gelatin, cellulose, carbohydrates such as lactose, glucose, saccharose or starch like corn starch, stearic acid and its salts such as magnesium stearate, talc, lanolin, petroleum jelly, or mixtures thereof, for example mixtures of water with one or more organic solvents such as mixtures of water with alcohols. The compounds of the formula I and their physiologically acceptable salts and solvates can also be lyophilized and the obtained lyophilisates used for the production of injectable compositions, for example.

The dosage of a compound of the formula I and/or a physiologically acceptable salt and/or solvate thereof to be administered depends on the specific case and, as is usual, has to be adapted by the physician according to the customary rules and procedures to the individual circumstances in order to achieve an optimum effect. It depends, for example, on the nature and the severity of the disorder to be treated, the sex, age, weight and individual responsiveness of the human or animal patient, on the efficacy and duration of action of the compound used, on whether the treatment is for the therapy of an acute or chronic disease or prophylactic, or on whether other active compounds are administered in addition to a compound of the formula I. In general, a daily dose from about 0.01 mg/kg to about 100 mg/kg, or from about 0.1 mg/kg to about 10 mg/kg, or from about 0.3 mg/kg to about 5 mg/kg (in each case mg per kg of bodyweight), for example, is appropriate for administration to an adult weighing about 75 kg in order to obtain the desired results. The daily dose can be administered in a single dose or, in particular when larger amounts are administered, divided into several, for example two, three or four, individual doses. The administration can also be carried out continuously, for example by continuous infusion or injection. Depending on the individual behavior in a specific case, it may be necessary to deviate upward or downward from the indicated dosages.

The examples below illustrate the invention.

When example compounds containing a basic group were purified by preparative high pressure liquid chromatography (HPLC) on reversed phase (RP) column material and, as customary, the eluent was a gradient mixture of water and acetonitrile containing trifluoroacetic acid (TFA), they were in part obtained in the form of their acid addition salt with trifluoroacetic acid, depending on the details of the workup such as evaporation or lyophilization conditions. In the names of the example compounds and their structural formulae any such trifluoroacetic acid present is not specified.

The prepared compounds were in general characterized by spectroscopic data and chromatographic data, in particular mass spectrum (MS) and HPLC retention times (Rt; in min) which were obtained by combined analytical HPLC/MS characterization (LC/MS), and/or nuclear magnetic resonance (NMR) spectra. In the NMR characterization, the chemical shift δ (in ppm), the number of hydrogen atoms and the multiplicity (s=singlet, d=doublet, dd=double doublet, t=triplet, dt=double triplet, q=quartet, m=multiplet; br=broad) of the signals is given. In the MS characterization, in general the mass number (m/z) of the peak of the molecular ion M, e.g. M$^+$, or of a related ion such as the ion M+1, e.g. [M+1]$^+$, i.e. the protonated molecular ion [M+H]$^+$, which was formed depending on the ionization method used, is given. Generally, the ionization method was electrospray ionization (ESI). The LC/MS conditions used were as follows.

Method LC1
Column: Phenomenex, 4 μM, 10×2 mm, 1.7 μm; flow rate: 1.1 ml/min; eluent A: water+0.05% trifluoroacetic acid; eluent B: acetonitrile; gradient: from 93% A+7% B to 5% A+95% B in 1.2 min, then 5% A+95% B for 0.2 min; MS ionization method: ESI$^+$ Method LC2
Column: UPLC BEH C18, 50×2.1 mm, 1.7 μm; flow rate: 0.9 ml/min; eluent A: water+0.1% formic acid; eluent B: acetonitrile+0.08% formic acid; gradient: from 95% A+5% B to 5% A+95% B in 1.1 min, then 5% A+95% B for 0.6 min; MS ionization method: ESI$^+$ Method LC3
Column: UPLC BEH C18, 50×2.1 mm, 1.7 μm; flow rate: 0.9 ml/min; eluent A: water+0.05% formic acid; eluent B: acetonitrile+0.035% formic acid; gradient: from 95% A+5% B to 5% A+95% B in 1.1 min, then 5% A+95% B for 0.6 min; MS ionization method: ESI$^+$ Method LC4
Column: Phenomenex, 4 μM, 10×2 mm, 1.7 μm; flow rate: 1.1 ml/min; eluent A: water+0.05% trifluoroacetic acid; eluent B: acetonitrile; gradient: from 80% A+20% B to 5% A+95% B in 0.8 min, then 5% A+95% B for 0.6 min; MS ionization method: ESI$^+$

EXAMPLE 1

{4-[5-(2,5-Difluorophenoxy)-7-propyloxazolo[5,4-d]pyrimidin-2-yl]-2,6-dimethylphenoxy}acetic acid

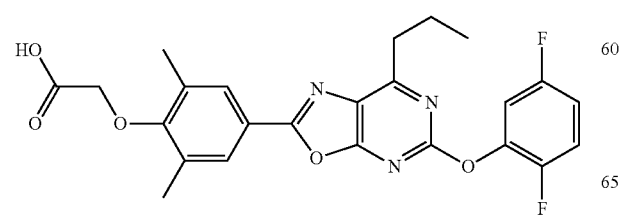

(a) Diethyl 2-(4-methoxy-3,5-dimethyl benzoylamino)malonate

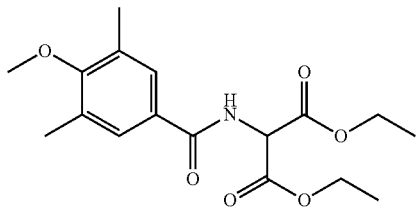 [SMILES: CCOC(=O)C(NC(=O)c1cc(C)c(OC)c(C)c1)C(=O)OCC]

58.4 g of diethyl aminomalonate hydrochloride were suspended in 300 ml of dichloromethane, and 115 ml of triethylamine were added with ice cooling. At 0° C., 54.8 g of 4-methoxy-3,5-dimethylbenzoyl chloride in 250 ml of dichloromethane were then added dropwise. After 2 hours at 0° C., 100 ml of water were added dropwise, and the aqueous phase was separated off and extracted with 200 ml of dichloromethane. The combined organic phases were extracted first with 2M aqueous hydrochloric acid and then with water, dried over sodium sulfate, filtered and concentrated. The residue was triturated with methyl tert-butyl ether, filtered off with suction and dried under reduced pressure. This gave 89.3 g (96%) of the title compound which was reacted further without any further purification.

LC/MS (Method LC1): Rt=0.94 min; m/z=338.10 [M+H]$^+$ (b) Sodium 4,6-dihydroxy-5-(4-methoxy-3,5-dimethylbenzoylamino)pyrimidine-2-thiolate

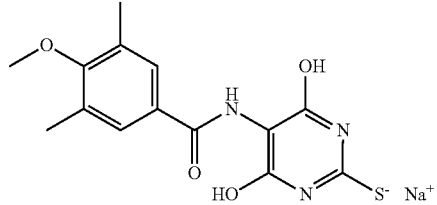 [SMILES: COc1c(C)cc(C(=O)Nc2c(O)nc([S-])nc2O)cc1C ; [Na+]]

20.6 g of thiourea were suspended in 900 ml of dry ethanol, and 75 ml of sodium methoxide solution (30% in methanol) were added. After 15 min, 91.0 g of diethyl 2-(4-methoxy-3,5-dimethylbenzoylamino)malonate were added a little at a time. Initially, this gave a clear solution, and soon a pale-yellow precipitate was formed. The reaction was then stirred at 60° C. for 3 hours. At room temperature, the precipitated solid was filtered off with suction and washed with about 100 ml of ethanol and then with diethyl ether, and dried under reduced pressure. This gave 78.3 g (84%) of the title compound which was reacted further without any further purification.

LC/MS (Method LC1): Rt=0.41 min; m/z=322.05 [M−Na+2H]$^+$ (c) N-(4,6-Dihydroxy-2-methylsulfanylpyrimidin-5-yl)-4-methoxy-3,5-dimethylbenzamide

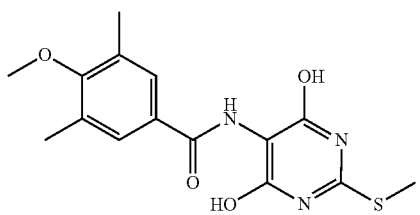

22.78 g of sodium hydroxide were initially charged in 735 ml of water, the mixture was cooled to 0° C., 78.21 g of sodium 4,6-dihydroxy-5-(4-methoxy-3,5-dimethylbenzoylamino)pyrimidine-2-thiolate and 365 ml of N-methyl-2-pyrrolidone were added and, after 30 min at 0° C., 14.2 ml of iodomethane were added dropwise. After 2 hours at 0° C., the reaction mixture was carefully adjusted to pH 2 using concentrated aqueous hydrochloric acid. About 200 ml of water were added, and the precipitated solid was filtered off with suction, washed with water until neutral and dried under reduced pressure. This gave 50.89 g (67%) of the title compound, which was reacted further without any further purification.

LC/MS (Method LC1): Rt=0.66 min; m/z=336.05 [M+H]$^+$ (d) 7-Chloro-2-(4-methoxy-3,5-dimethylphenyl)-5-methylsulfanyloxazolo[5,4-d]pyrimidine

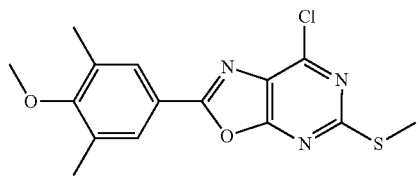

At room temperature, 45.95 g of N-(4,6-dihydroxy-2-methylsulfanylpyrimidin-5-yl)-4-methoxy-3,5-dimethylbenzamide were suspended with stirring in 125 ml of phosphorus oxychloride, and the mixture was heated at 70° C. for 36 hours. After cooling, the reaction mixture was sucked through a glass frit, giving a yellow solid which was introduced with stirring into a saturated aqueous sodium bisulfate solution and stirred for 10 min. The solid was then filtered off with suction, washed until neutral and dried. This gave 10.47 g (22%) of the title compound, which was reacted further without any further purification.

LC/MS (Method LC4): Rt=0.88 min; m/z=336.00 [M+H]$^+$ (e) 4-(7-Chloro-5-methylsulfanyloxazolo[5,4-d]pyrimidin-2-yl)-2,6-dimethylphenol

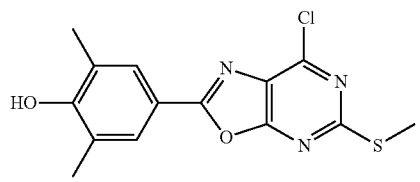 [SMILES: CSc1nc(Cl)c2nc(-c3cc(C)c(O)c(C)c3)oc2n1]

At −20° C., 5.30 g of boron tribromide were added dropwise with stirring to a solution of 6.72 g of 7-chloro-2-(4-methoxy-3,5-dimethylphenyl)-5-methylsulfanyloxazolo[5,4-d]pyrimidine in 140 ml of dichloromethane. The reaction mixture was allowed to warm to room temperature and stirred for 2 hours. With ice cooling, another 1.33 g of boron tribromide were then added dropwise. After a further 2 hours, the reaction was once more cooled to −20° C., and sat. aqueous sodium bicarbonate solution was carefully added dropwise. The phases were separated at room temperature. The organic phase was washed with water, dried over sodium sulfate, filtered and concentrated under reduced pressure. The residue was triturated with diisopropyl ether, filtered off with suction and air-dried. This gave 6.20 g (96%) of the title compound, which was reacted further without any further purification.

LC/MS (Method LC1): Rt=1.12 min; m/z=322.10 [M+H]$^+$ (f) tert-Butyl [4-(7-chloro-5-methylsulfanyloxazolo[5,4-d]pyrimidin-2-yl)-2,6-dimethylphenoxy]acetate

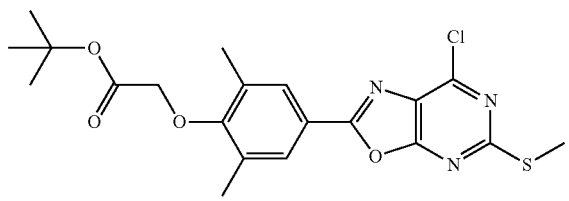 [SMILES: CSc1nc(Cl)c2nc(-c3cc(C)c(OCC(=O)OC(C)(C)C)c(C)c3)oc2n1]

7.46 g of potassium carbonate were added to a solution of 4.34 g of 4-(7-chloro-5-methylsulfanyloxazolo[5,4-d]pyrimidin-2-yl)-2,6-dimethylphenol in 45 ml of dimethylformamide, and 2.90 g of tert-butyl bromoacetate were then added. The mixture was stirred at 60° C. for 1 h. The cooled reaction mixture was then added to ice water, and the precipitated solid was filtered off with suction and washed with water. The solid was taken up in dichloromethane and dried over sodium sulfate, activated carbon was added and the mixture was filtered and concentrated under reduced pressure. This gave 4.20 g (71%) of the title compound, which was reacted further without any further purification.

LC/MS (Method LC1): Rt=1.28 min; m/z=436.10 [M+H]$^+$ (g) tert-Butyl [2,6-dimethyl-4-(5-methylsulfanyl-7-propyloxazolo[5,4-d]pyrimidin-2-yl)phenoxy]acetate

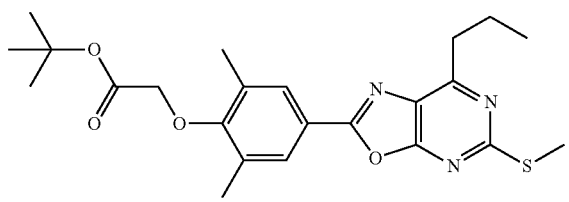 [SMILES: CCCc1nc(SC)nc2oc(-c3cc(C)c(OCC(=O)OC(C)(C)C)c(C)c3)nc12]

Under argon and at −78° C., 1.38 ml of a 2.0 M solution of n-propylmagnesium bromide in tetrahydrofuran were slowly added dropwise to a solution of 1.09 g of tert-butyl [4-(7-chloro-5-methylsulfanyloxazolo[5,4-d]pyrimidin-2-yl)-2,6-dimethylphenoxy]acetate and 44 mg of iron(III) acetylacetonate in 100 ml of dry tetrahydrofuran. The reaction was allowed to warm to room temperature over a period of one hour and stirred for another two hours. Diethyl ether was then added to the reaction mixture, and 10% strength aqueous sodium bisulfate solution was added with ice cooling. The phases were separated, and the aqueous phase was extracted twice with diethyl ether. The combined organic phase was washed with water, dried over sodium sulfate, filtered and concentrated under reduced pressure. The crude product gave, after chromatography on silica gel (heptanes/ethyl acetate), 0.11 g (10%) of the title compound.

LC/MS (Method LC2): Rt=1.55 min; m/z=444.20 [M+H]$^+$ (h) tert-Butyl [4-(5-methanesulfonyl-7-propyloxazolo[5,4-d]pyrimidin-2-yl)-2,6-dimethylphenoxy]acetate

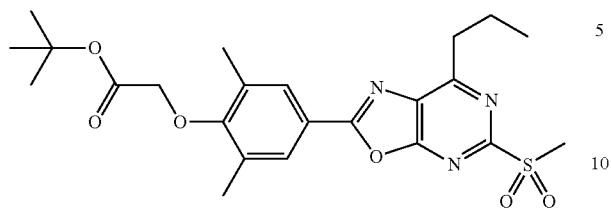

105 mg of tert-butyl [2,6-dimethyl-4-(5-methylsulfanyl-7-propyloxazolo[5,4-d]pyrimidin-2-yl)phenoxy]acetate were initially charged in 1.2 ml of dichloromethane, and 128 mg of 3-chloroperbenzoic acid were added at room temperature. After 1 h, the reaction was diluted with dichloromethane and washed twice with 1M aqueous sodium hydroxide solution, then with sat. aqueous sodium sulfite solution and finally with water. The org. phase was dried over sodium sulfate, filtered and concentrated, giving 107 mg (98%) of the title compound, which was reacted further without any further purification.

LC/MS (Method LC2): Rt=1.41 min; m/z=476.30 [M+H]$^+$ (i) tert-Butyl {4-[5-(2,5-difluorophenoxy)-7-propyloxazolo[5,4-d]pyrimidin-2-yl]-2,6-dimethylphenoxy}acetate

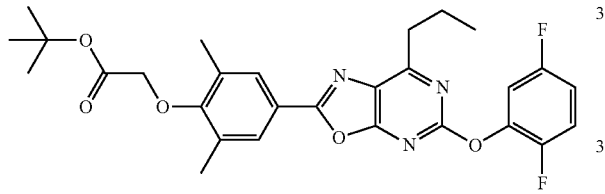

68 mg of potassium carbonate were added to a solution of 107 mg of tert-butyl [4-(5-methanesulfonyl-7-propyloxazolo[5,4-d]pyrimidin-2-yl)-2,6-dimethylphenoxy]acetate in 1.1 ml of NMP, and 32 mg of 2,5-difluorophenol were then added. The reaction mixture was heated in a microwave synthesizer to 110° C. for 5 min and then cooled and poured onto ice. The precipitated compound was taken up in ethyl acetate, washed with water until neutral, dried over sodium sulfate, filtered and concentrated. The crude product was chromatographed on silica gel (heptane/ethyl acetate), giving 45 mg (38%) of the title compound.

LC/MS (Method LC2): Rt=1.53 min; m/z=526.30 [M+H]$^+$ (j) {4-[5-(2,5-Difluorophenoxy)-7-propyloxazolo[5,4-d]pyrimidin-2-yl]-2,6-dimethylphenoxy}acetic acid

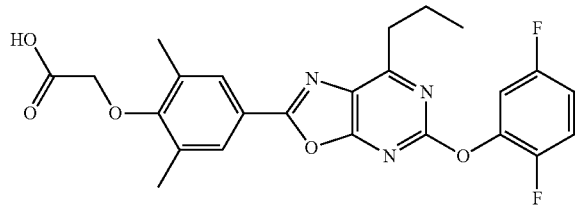 [SMILES: CCCc1nc(Oc2cc(F)ccc2F)nc2oc(-c3cc(C)c(OCC(=O)O)c(C)c3)nc12]

55 µl of trifluoroacetic acid were added to a solution of 39 mg of tert-butyl {-4-[5-(2,5-difluorophenoxy)-7-propyloxazolo[5,4-d]pyrimidin-2-yl]-2,6-dimethylphenoxy}acetate in 0.4 ml of dichloromethane, and the mixture was stirred at room temperature for 16 h. The reaction was then concentrated under reduced pressure, and the residue was triturated with diisopropyl ether, filtered off with suction and dried. This gave 21 mg (60%) of the title compound.

LC/MS (Method LC2): Rt=1.38 min; m/z=470.20 [M+H]$^+$

EXAMPLE 2

{2,6-Dimethyl-4-[7-propyl-5-(3,3,3-trifluoropropoxy)oxazolo[5,4-d]pyrimidin-2-yl]phenoxy}acetic acid

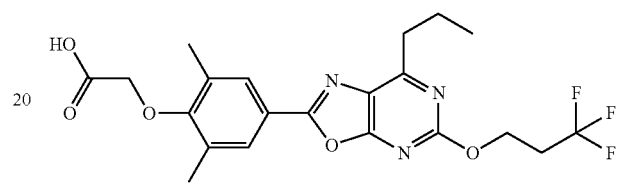

(a) tert-Butyl {2,6-dimethyl-4-[7-propyl-5-(3,3,3-trifluoropropoxy)oxazolo[5,4-d]pyrimidin-2-yl]phenoxy}acetate

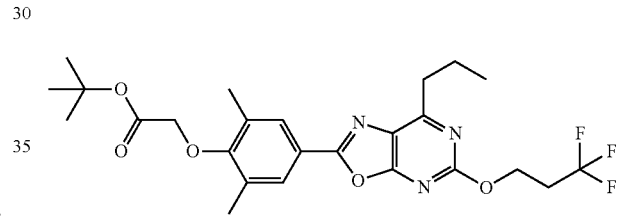

116 mg of 3,3,3-trifluoropropan-1-ol were added to 46 mg of sodium hydride (60% pure in mineral oil) in 1.5 ml of dry N,N-dimethylformamide. After 5 min, 111 mg of tert-butyl [4-(5-methanesulfonyl-7-propyloxazolo[5,4-d]pyrimidin-2-yl)-2,6-dimethylphenoxy]acetate were added, and the reaction was stirred initially at room temperature for 2 h and then at 80° C. for 15 min. For work-up, saturated aqueous citric acid solution was added, and the reaction was extracted three times with ethyl acetate. The combined organic phases were washed with water, dried over sodium sulfate, filtered and concentrated under reduced pressure. Purification by preparative HPLC gave 12 mg (10%) of the title compound.

LC/MS (Method LC4): Rt=0.93 min; m/z=510.25 [M+H]$^+$ (b) {2,6-Dimethyl-4-[7-propyl-5-(3,3,3-trifluoropropoxy)oxazolo[5,4-d]pyrimidin-2-yl]phenoxy}acetic acid

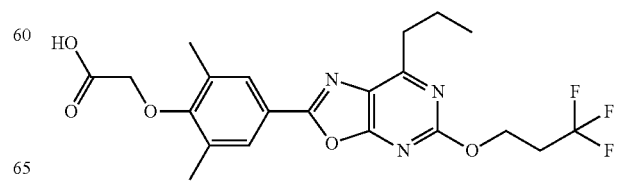

Analogously to example 1 (j), the reaction of 12 mg of tert-butyl {2,6-dimethyl-4-[7-propyl-5-(3,3,3-trifluoropropoxy)oxazolo[5,4-d]pyrimidin-2-yl]phenoxy}acetate with trifluoroacetic acid gave 11 mg (83%) of the title compound.

LC/MS (Method LC2): Rt=1.36 min; m/z=454.10 [M+H]+

EXAMPLE 3

{4-[5-(2-Fluorophenoxy)-7-isobutyloxazolo[5,4-d]pyrimidin-2-yl]-2,6-dimethylphenoxy}acetic acid

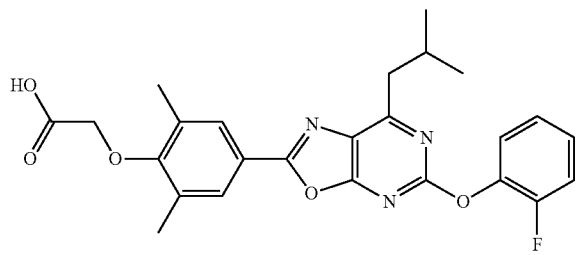 [SMILES: Cc1cc(-c2nc3c(CC(C)C)nc(Oc4ccccc4F)nc3o2)cc(C)c1OCC(=O)O]

(a) tert-Butyl [4-(7-isobutyl-5-methylsulfanyloxazolo[5,4-d]pyrimidin-2-yl)-2,6-dimethylphenoxy]acetate

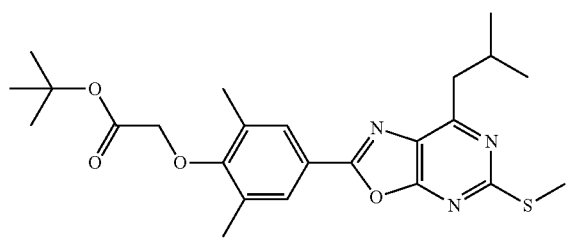 [SMILES: CSc1nc(CC(C)C)c2nc(-c3cc(C)c(OCC(=O)OC(C)(C)C)c(C)c3)oc2n1]

Analogously to example 1 (g), the reaction of 1.50 g of tert-butyl [4-(7-chloro-5-methylsulfanyloxazolo[5,4-d]pyrimidin-2-yl)-2,6-dimethylphenoxy]acetate with isobutylmagnesium bromide gave 0.31 g (20%) of the title compound.

LC/MS (Method LC2): Rt=1.44 min; m/z=458.30 [M+H]+

(b) tert-Butyl [4-(7-isobutyl-5-methanesulfonyloxazolo[5,4-d]pyrimidin-2-yl)-2,6-dimethylphenoxy]acetate

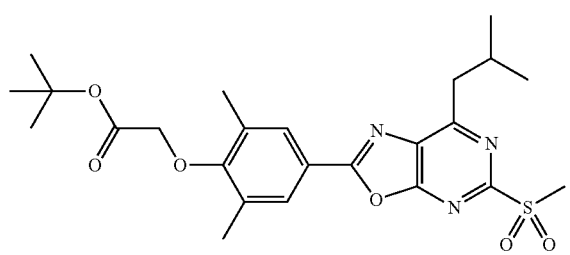 [SMILES: Cc1cc(-c2nc3c(CC(C)C)nc(S(C)(=O)=O)nc3o2)cc(C)c1OCC(=O)OC(C)(C)C]

Analogously to example 1 (h), the reaction of 0.31 g of tert-butyl [4-(7-isobutyl-5-methylsulfanyloxazolo[5,4-d]pyrimidin-2-yl)-2,6-dimethylphenoxy]acetate with 3-chloroperbenzoic acid gave 0.31 g (93%) of the title compound.

LC/MS (Method LC2): Rt=1.43 min; m/z=490.20 [M+H]+

(c) tert-Butyl {4-[5-(2-fluorophenoxy)-7-isobutyloxazolo[5,4-d]pyrimidin-2-yl]-2,6-dimethylphenoxy}acetate

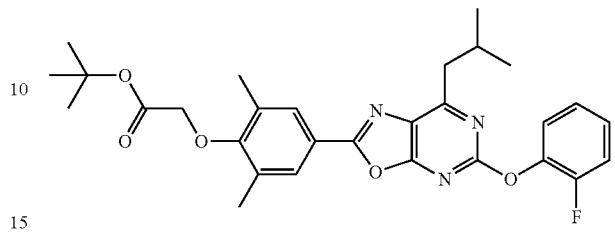

Analogously to example 1 (i), the reaction of 60 mg of tert-butyl [4-(7-isobutyl-5-methanesulfonyloxazolo[5,4-d]pyrimidin-2-yl)-2,6-dimethylphenoxy]acetate with 2-fluorophenol gave 64 mg (100%) of the title compound.

LC/MS (Method LC4): Rt=1.01 min; m/z=522.25 [M+H]+

(d) {4-[5-(2-Fluorophenoxy)-7-isobutyloxazolo[5,4-d]pyrimidin-2-yl]-2,6-dimethylphenoxy}acetic acid

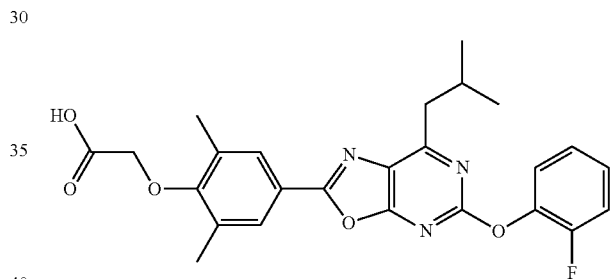

Analogously to example 1 (j), the reaction of 64 mg of tert-butyl {4-[5-(2-fluorophenoxy)-7-isobutyloxazolo[5,4-d]pyrimidin-2-yl]-2,6-dimethylphenoxy}acetate with trifluoroacetic acid gave 33 mg (56%) of the title compound.

LC/MS (Method LC2): Rt=1.40 min; m/z=466.20 [M+H]+

EXAMPLE 4

{4-[7-Isobutyl-5-(3,3,3-trifluoropropoxy)oxazolo[5,4-d]pyrimidin-2-yl]-2,6-dimethylphenoxy}acetic acid

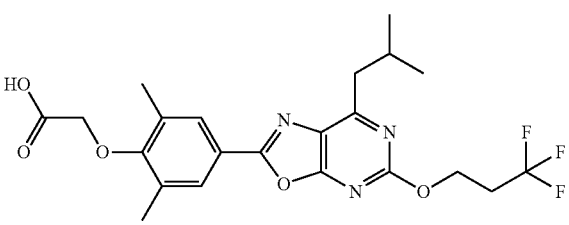 [SMILES: Cc1cc(-c2nc3c(CC(C)C)nc(OCCC(F)(F)F)nc3o2)cc(C)c1OCC(=O)O]

(a) tert-Butyl {4-[7-isobutyl-5-(3,3,3-trifluoropropoxy)oxazolo[5,4-d]pyrimidin-2-yl]-2,6-dimethylphenoxy}acetate

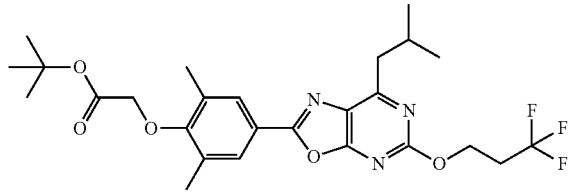 [SMILES: Cc1cc(-c2nc3c(CC(C)C)nc(OCCC(F)(F)F)nc3o2)cc(C)c1OCC(=O)OC(C)(C)C]

Analogously to example 2 (a), the reaction of 95 mg of tert-butyl [4-(7-isobutyl-5-methanesulfonyloxazolo[5,4-d]pyrimidin-2-yl)-2,6-dimethylphenoxy]acetate with 3,3,3-trifluoropropan-1-ol gave 10 mg (10%) of the title compound.

LC/MS (Method LC4): Rt=0.96 min; m/z=524.25 [M+H]+

(b) {4-[7-Isobutyl-5-(3,3,3-trifluoropropoxy)oxazolo[5,4-d]pyrimidin-2-yl]-2,6-dimethylphenoxy}acetic acid

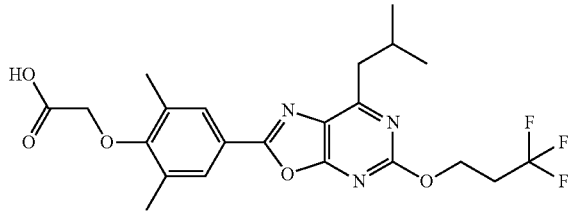 [SMILES: Cc1cc(-c2nc3c(CC(C)C)nc(OCCC(F)(F)F)nc3o2)cc(C)c1OCC(=O)O]

Analogously to example 1 (j), the reaction of 8 mg of tert-butyl {4-[7-isobutyl-5-(3,3,3-trifluoropropoxy)oxazolo[5,4-d]pyrimidin-2-yl]-2,6-dimethylphenoxy}acetate with trifluoroacetic acid gave 4 mg (56%) of the title compound.

LC/MS (Method LC4): Rt=0.80 min; m/z=468.15 [M+H]+

EXAMPLE 5

{4-[5-(3-Chlorophenoxy)-7-isobutyloxazolo[5,4-d]pyrimidin-2-yl]-2,6-dimethylphenoxy}acetic acid

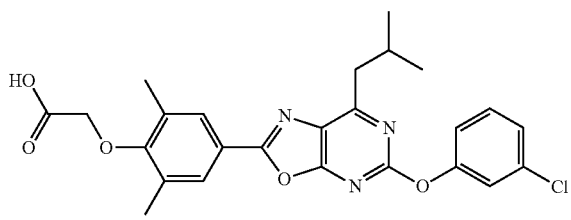 [SMILES: Cc1cc(-c2nc3c(CC(C)C)nc(Oc4cccc(Cl)c4)nc3o2)cc(C)c1OCC(=O)O]

(a) tert-Butyl {4-[5-(3-chlorophenoxy)-7-isobutyloxazolo[5,4-d]pyrimidin-2-yl]-2,6-dimethylphenoxy}acetate

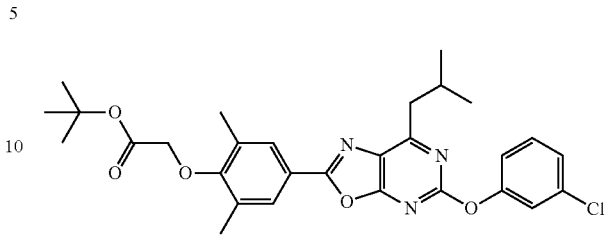

Analogously to example 1 (i), the reaction of 60 mg of tert-butyl [4-(7-isobutyl-5-methanesulfonyloxazolo[5,4-d]pyrimidin-2-yl)-2,6-dimethylphenoxy]acetate with 3-chlorophenol gave 65 mg (100%) of the title compound.

LC/MS (Method LC4): Rt=1.04 min; m/z=538.25 [M+H]+

(b) {4-[5-(3-Chlorophenoxy)-7-isobutyloxazolo[5,4-d]pyrimidin-2-yl]-2,6-dimethylphenoxy}acetic acid

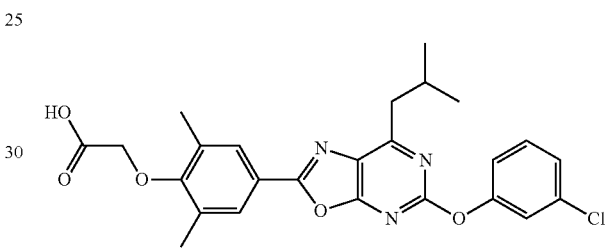

Analogously to example 1 (j), the reaction of 62 mg of tert-butyl {4-[5-(3-chlorophenoxy)-7-isobutyloxazolo[5,4-d]pyrimidin-2-yl]-2,6-dimethylphenoxy}acetate with trifluoroacetic acid gave 31 mg (45%) of the title compound.

LC/MS (Method LC2): Rt=1.44 min; m/z=482.14 [M+H]+

EXAMPLE 6

{4-[5-(3-Chlorophenoxy)-7-propyloxazolo[5,4-d]pyrimidin-2-yl]-2,6-dimethylphenoxy}acetic acid

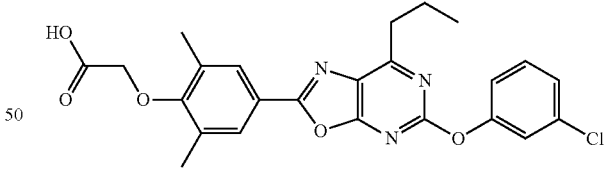

(a) tert-Butyl {4-[5-(3-chlorophenoxy)-7-propyloxazolo[5,4-d]pyrimidin-2-yl]-2,6-dimethylphenoxy}acetate

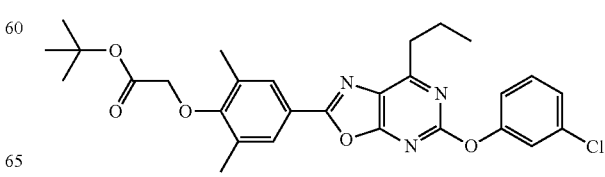

Analogously to example 1 (i), the reaction of 104 mg of tert-butyl [4-(5-methanesulfonyl-7-propyloxazolo[5,4-d]pyrimidin-2-yl)-2,6-dimethylphenoxy]acetate with 3-chlorophenol gave 115 mg (100%) of the title compound.
LC/MS (Method LC2): Rt=1.42 min; m/z=524.30 [M+H]$^+$ (b) {4-[5-(3-Chlorophenoxy)-7-propyloxazolo[5,4-d]pyrimidin-2-yl]-2,6-dimethylphenoxy}acetic acid

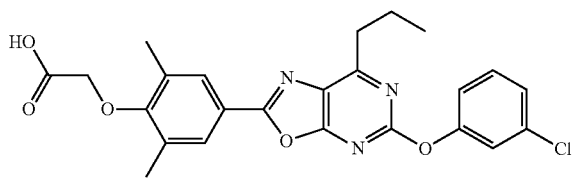 [SMILES: CCCc1nc(Oc2cccc(Cl)c2)nc2oc(-c3cc(C)c(OCC(=O)O)c(C)c3)nc12]

Analogously to example 1 (j), the reaction of 115 mg of tert-butyl {4-[5-(3-chlorophenoxy)-7-propyloxazolo[5,4-d]pyrimidin-2-yl]-2,6-dimethylphenoxy}acetate with trifluoroacetic acid gave 44 mg (43%) of the title compound.
LC/MS (Method LC2): Rt=1.29 min; m/z=468.20 [M+H]$^+$

EXAMPLE 7

{4-[5-(4-Chlorobenzyl)-7-isobutyloxazolo[5,4-d]pyrimidin-2-yl]-2,6-dimethylphenoxy}acetic acid

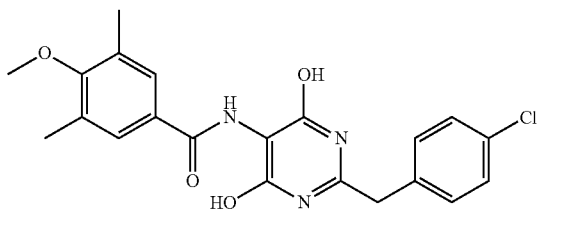 [SMILES: COc1c(C)cc(C(=O)Nc2c(O)nc(Cc3ccc(Cl)cc3)nc2O)cc1C]

(a) N-[2-(4-Chlorobenzyl)-4,6-dihydroxypyrimidin-5-yl]-4-methoxy-3,5-dimethylbenzamide

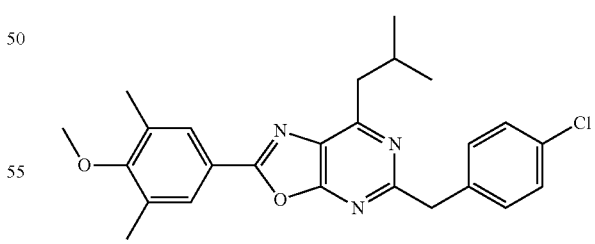

25.6 g of 2-(4-chlorophenyl)acetamidine hydrochloride were dissolved in 425 ml of dry ethanol, and 70 ml of sodium methoxide were added. After 15 min, 42.2 g of 2-diethyl (4-methoxy-3,5-dimethylbenzoylamino)malonate were added a little at a time, and the reaction was then stirred at 80° C. for 2 h. After cooling to room temperature, the precipitated solid was filtered off with suction, washed with a little ethanol and tetrahydrofuran and dried under reduced pressure.
This gave 41.5 g (85%) of the title compound, which was reacted further without any further purification.
LC/MS (Method LC1): Rt=0.81 min; m/z=414.1 [M+H]$^+$ (b) 5-(4-Chlorobenzyl)-2-(4-methoxy-3,5-dimethylphenyl)oxazolo[5,4-d]pyrimidin-7-ol

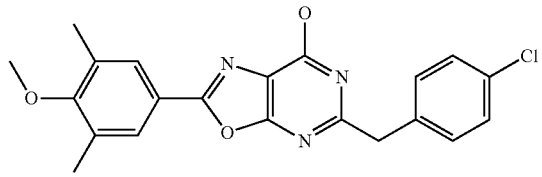 [SMILES: COc1c(C)cc(-c2nc3c(O)nc(Cc4ccc(Cl)cc4)nc3o2)cc1C]

40 g of N-[2-(4-chlorobenzyl)-4,6-dihydroxypyrimidin-5-yl]-4-methoxy-3,5-dimethylbenzamide and 150 ml of phosphorus oxychloride were heated at 70° C. for 1.5 h. The mixture was then allowed to cool. The solid formed was filtered off with suction, washed with diethyl ether and dried. This gave 21.1 g (55%) of the title compound.
LC/MS (Method LC2): Rt=1.24 min; m/z=396.0 [M+H]$^+$ (c) 7-Chloro-5-(4-chlorobenzyl)-2-(4-methoxy-3,5-dimethylphenyl)oxazolo[5,4-d]pyrimidine

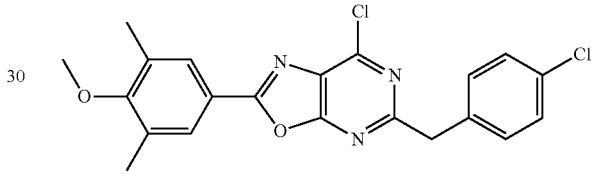

10 g of 5-(4-chlorobenzyl)-2-(4-methoxy-3,5-dimethylphenyl)oxazolo[5,4-d]pyrimidin-7-ol and 50 ml of phosphorus oxychloride were heated at 90° C. for 5 h. The mixture was then allowed to cool. The solid formed was filtered off with suction, washed with diethyl ether and dried. This gave 10.4 g (99%) of the title compound.
LC/MS (Method LC2): Rt=1.09 min; m/z=414.1 [M+H]$^+$ (d) 5-(4-Chlorobenzyl)-7-isobutyl-2-(4-methoxy-3,5-dimethylphenyl)oxazolo[5,4-d]pyrimidine Under argon and at 0° C., 2.0 ml of a 2.0 M solution of isobutylmagnesium bromide in tetrahydrofuran were slowly added dropwise to a degassed solution of 1.50 g of 7-chloro-5-(4-chlorobenzyl)-2-(4-methoxy-3,5-dimethylphenyl)oxazolo[5,4-d]pyrimidine and 65 mg of iron(III) acetylacetonate in 20 ml of dry tetrahydrofuran. After 15 min at 0° C., diethyl ether was added to the reaction mixture, and 10% strength aqueous citric acid solution was added with ice cooling. The phases were separated, and the aqueous phase was extracted twice with diethyl ether. The combined organic phases was washed with water, dried over sodium sulfate, filtered and concentrated under reduced pressure. From the crude product, 0.80 g (51%) of the title compound was isolated after reprecipitation from acetonitrile.

LC/MS (Method LC2): Rt=1.60 min; m/z=436.17 [M+H]$^+$ (e) 4-[5-(4-Chlorobenzyl)-7-isobutyloxazolo[5,4-d]pyrimidin-2-yl]-2,6-dimethylphenol

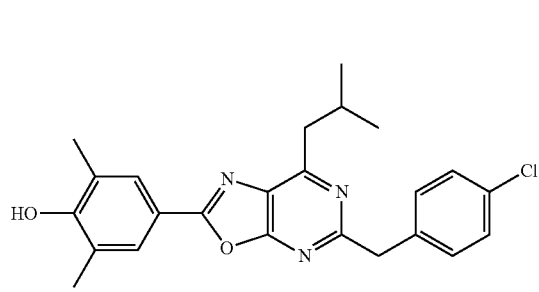 [SMILES: Cc1cc(-c2nc3c(CC(C)C)nc(Cc4ccc(Cl)cc4)nc3o2)cc(C)c1O]

Analogously to example 1 (e), the reaction of 850 mg of 5-(4-chlorobenzyl)-7-isobutyl-2-(4-methoxy-3,5-dimethylphenyl)oxazolo[5,4-d]pyrimidine with boron tribromide gave 690 mg (84%) of the title compound.

LC/MS (Method LC2): Rt=1.51 min; m/z=422.16 [M+H]$^+$ (f) tert-Butyl {4-[5-(4-chlorobenzyl)-7-isobutyloxazolo[5,4-d]pyrimidin-2-yl]-2,6-dimethylphenoxy}acetate

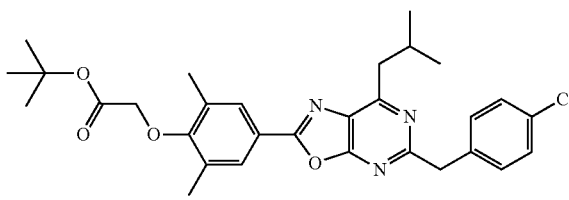 [SMILES: Cc1cc(-c2nc3c(CC(C)C)nc(Cc4ccc(Cl)cc4)nc3o2)cc(C)c1OCC(=O)OC(C)(C)C]

Analogously to example 1 (f), the reaction of 684 mg of 4-[5-(4-chlorobenzyl)-7-isobutyloxazolo[5,4-d]pyrimidin-2-yl]-2,6-dimethylphenol with tert-butyl bromoacetate gave 800 mg (92%) of the title compound.

LC/MS (Method LC2): Rt=1.62 min; m/z=536.22 [M+H]$^+$ (g) {4-[5-(4-Chlorobenzyl)-7-isobutyloxazolo[5,4-d]pyrimidin-2-yl]-2,6-dimethylphenoxy}acetic acid

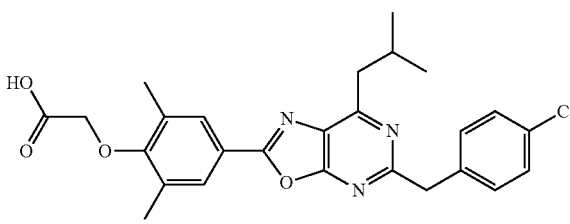

Analogously to example 1 (j), the reaction of 784 mg of tert-butyl {4-[5-(4-chlorobenzyl)-7-isobutyloxazolo[5,4-d]pyrimidin-2-yl]-2,6-dimethylphenoxy}acetate with trifluoroacetic acid gave 702 mg (100%) of the title compound.

LC/MS (Method LC2): Rt=1.47 min; m/z=480.16 [M+H]$^+$

EXAMPLE 8

[4-(5-Benzyl-7-isobutyloxazolo[5,4-d]pyrimidin-2-yl)-2,6-dimethylphenoxy]acetic acid

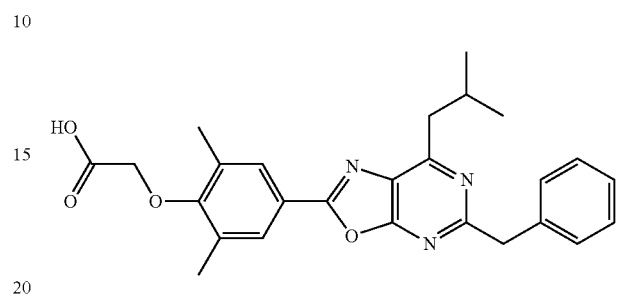

10 mg of palladium on carbon (10%) were added to a solution of 50 mg of {4-[5-(4-chlorobenzyl)-7-isobutyloxazolo[5,4-d]pyrimidin-2-yl]-2,6-dimethylphenoxy}acetic acid, and the mixture was hydrogenated at 5 bar overnight. Three times, another 10 mg of palladium on carbon (10%) were added and the mixture was in each case hydrogenated for a day. For work-up, the catalyst was filtered off through Celite and the solution obtained was concentrated. The residue was purified by HPLC. This gave 7 mg (18%) of the title compound.

LC/MS (Method LC2): Rt=1.43 min; m/z=446.30 [M+H]$^+$

EXAMPLE 9

{4-[5-(4-Chlorobenzyl)-7-isopropyloxazolo[5,4-d]pyrimidin-2-yl]-2,6-dimethylphenoxy}acetic acid

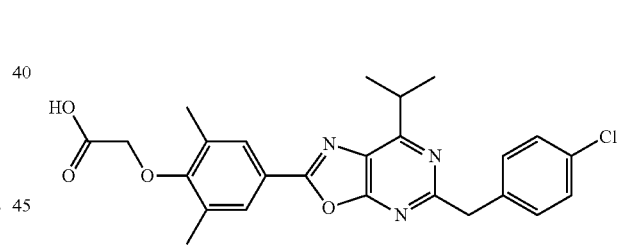

(a) 5-(4-Chlorobenzyl)-7-isopropyl-2-(4-methoxy-3,5-dimethylphenyl)oxazolo[5,4-d]pyrimidine

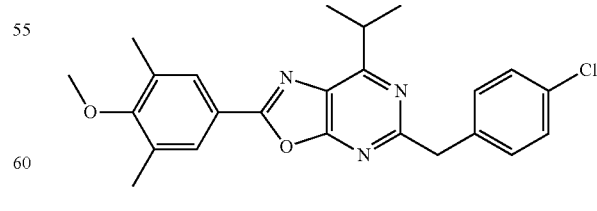

Analogously to example 7 (d), the reaction of 1.5 g of 7-chloro-5-(4-chlorobenzyl)-2-(4-methoxy-3,5-dimethylphenyl)oxazolo[5,4-d]pyrimidine with isopropylmagnesium bromide gave 165 mg (11%) of the title compound.

LC/MS (Method LC2): Rt=1.60 min; m/z=422.16 [M+H]$^+$ (b) 4-[5-(4-Chlorobenzyl)-7-isopropyloxazolo[5,4-d]pyrimidin-2-yl]-2,6-dimethylphenol

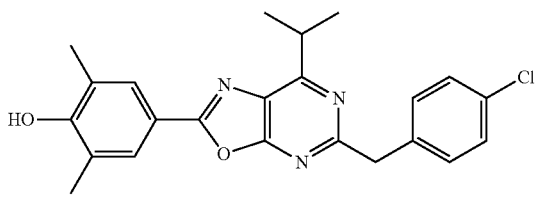 [SMILES: Cc1cc(-c2nc3c(C(C)C)nc(Cc4ccc(Cl)cc4)nc3o2)cc(C)c1O]

Analogously to example 1 (e), the reaction of 170 mg of 5-(4-chlorobenzyl)-7-isopropyl-2-(4-methoxy-3,5-dimethylphenyl)oxazolo[5,4-d]pyrimidine with boron tribromide gave 115 mg (70%) of the title compound.
LC/MS (Method LC2): Rt=1.50 min; m/z=408.14 [M+H]$^+$ (c) tert-Butyl {4-[5-(4-chlorobenzyl)-7-isopropyloxazolo[5,4-d]pyrimidin-2-yl]-2,6-dimethylphenoxy}acetate

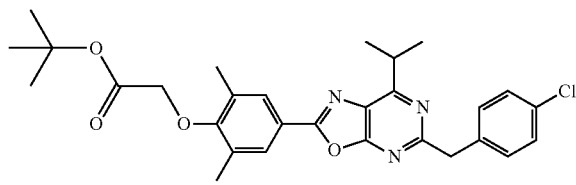 [SMILES: Cc1cc(-c2nc3c(C(C)C)nc(Cc4ccc(Cl)cc4)nc3o2)cc(C)c1OCC(=O)OC(C)(C)C]

Analogously to example 1 (f), the reaction of 80 mg of 4-[(5-(4-chlorobenzyl)-7-isopropyloxazolo[5,4-d]pyrimidin-2-yl]-2,6-dimethylphenol with tert-butyl bromoacetate gave 67 mg (65%) of the title compound.
LC/MS (Method LC4): Rt=1.15 min; m/z=522.15 [M+H]$^+$ (d) {4-[5-(4-Chlorobenzyl)-7-isopropyloxazolo[5,4-d]pyrimidin-2-yl]-2,6-dimethylphenoxy}acetic acid

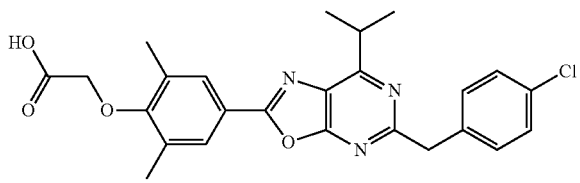 [SMILES: Cc1cc(-c2nc3c(C(C)C)nc(Cc4ccc(Cl)cc4)nc3o2)cc(C)c1OCC(=O)O]

Analogously to example 1 (j), the reaction of 67 mg of tert-butyl {4-[5-(4-chlorobenzyl)-7-isopropyloxazolo[5,4-d]pyrimidin-2-yl]-2,6-dimethylphenoxy}acetate with trifluoroacetic acid gave 74 mg (100%) of the title compound.
LC/MS (Method LC2): Rt=1.47 min; m/z=466.2 [M+H]$^+$ Determination of the Pharmacological Activity A) GTP-γ-S Assay Using Human Edg-1 Receptors In order to determine the Edg-1 receptor activation by the compounds of the invention, a GTP-γ-S (GTP-γ-S=guanosine 5'-[thio]triphosphate) assay for G-protein coupled receptor binding based on the scintillation proximity assay principle was used, employing a cell membrane preparation from a CHO Flp-In cell line which constitutively overexpresses the human Edg-1 receptor.

(a) Cell Line Generation

The Flp-In™ expression system (Invitrogen, cat. no. K6010-01) allows the generation of stable mammalian cell lines into which the gene of interest has been integrated through homologous recombination at a specific genomic location called Flp Recombination Target (FRT) site by means of an Flp recombinase encoded by the pOG44 expression plasmid. The integration of the pcDNA5/FRT expression construct into the Flp-In host cell line genome results in the transcription of the gene of interest. The stably transfected cells become hygromycin-resistant.

One day prior to transfection, 200 000 Flp-In-CHO cells were seeded in Ham F-12 medium (Invitrogen, cat. no. 31765) supplemented with 10% fetal calf serum (FCS; Perbio Science, cat. no. SH30068.03) in a 6-well plate and incubated at 37° C./5% $CO_2$ overnight. Using the FuGENE® 6 transfection reagent (Roche, cat. no. 11988387001), cells were cotransfected with the Flp recombinase expression plasmid pOG44 and a modified plasmid additionally containing the edg-1 gene (accession no. NM_001400) termed as pcDNA5-FRT-TO_nFLAG_DEST-EDG-1 with a 9:1 ratio. To obtain the modified pcDNA5-FRT-TO_nFLAG_DEST plasmid, the Invitrogen plasmid pcDNA5/FRT/TO (Invitrogen, cat. no. V6520-20) was adapted to the Gateway® (Invitrogen) cloning system by inserting a Gateway cassette containing attR recombination sites flanking a ccdB gene and a chloramphenicol-resistance gene (Gateway Conversion System, Invitrogen, cat. no. 11828-029). In addition a FLAG tag epitope was added before the 5' att recombination site to allow recombinant expression of N-terminally FLAG-tagged proteins.

For the transfection of one well, 1.08 µg of pOG44 and 0.12 µg of pcDNA5-FRT-TO_nFLAG_DEST-EDG-1 were mixed to 100 µl of serum-free Ham F-12 medium containing 6 µl of FuGENE® 6 transfection reagent. After 20 min of incubation, the transfection reagent/DNA complex was distributed dropwise on the cells. The cells were incubated for 24 h at 37° C. Then the cells from 3 wells were transferred to a T75 flask (Greiner Cellstar®, cat. no. 658175) containing Ham F-12 medium supplemented with 10% of FCS but without antibiotic and were incubated another 24 h. 48 h after transfection, the medium was replaced by selection medium (Ham F-12 supplemented with 10% of FCS and 300 µg/ml of hygromycin B (Invitrogen, cat. no. 10687-010)). The medium was exchanged every 2 to 3 days until a resistant population of cells had grown. Cells were several times splitted and seeded into a new flask so that the cells did not reach more than 25% of confluency. After 2 weeks of selection, the cells were transferred into T175 flasks (Greiner Cellstar®, cat. no. 660175) and cultivated for batch production. Cells were harvested from the culture flasks by short treatment (2 to 5 min) with Accutase (PAA, cat. no. L11-007), resuspended in selection medium (see above) and centrifuged at 200×g for 5 min. Cells were resuspended in a mixture of 90% of FCS and 10% of dimethyl sulfoxide and stored frozen in liquid nitrogen.

(b) Membrane Preparation

A membrane preparation was obtained by standard methods from the aforedescribed CHO Flp-In cell line constitutively overexpressing the human Edg-1 receptor. Briefly, the cryopreserved cells were taken in culture and grown until confluency in T175 cell culture flasks (Becton Dickinson, cat. no. 35 5001). Cell culture was stopped by washing with calcium-free phosphate-buffered saline (PBS; Gibco, cat. no. 14190), and cells were harvested with a rubber-policeman in 4° C. cold and calcium-free PBS supplemented with a protease inhibitor cocktail (complete protease inhibitor; Roche, cat. no. 1697498; 1 tablet per 50 ml) and subsequently centrifuged at 4° C. for 15 min at 1100×g (Heraeus Minifuge T). For cell lysis, the pellet was resuspended in a 4° C. cold hypotonic buffer consisting of 5 mM HEPES (Sigma-Aldrich, cat. no. H-0981), 1 mM EDTA (disodium salt; Merck, cat. no. 8418) supplemented with protease inhibitor cocktail (as above) in which cells were stored for another 15 min on ice. After lysis, cells were centrifuged at 4° C. for 10 min at 400×g (Heraeus Minifuge T). The pellet was disrupted in a Dounce homogenizer, diluted with the supernatant of the previous centrifugation and subsequently centrifuged at 4° C. for 10 min at 500×g (Heraeus Minifuge T) in order to separate nuclei and still intact cells from the membranes mainly present in the supernatant. The supernatant was then diluted in hypotonic buffer and centrifuged (Beckmann, Avanti J251) at approximately 18600×g for 2 h at 4° C. After centrifugation, the membrane pellet was resuspended in a storing buffer consisting of 20 mM HEPES; 150 mM NaCl (Merck, cat. no. 6400), 1 mM EDTA (as above) supplemented with protease inhibitor cocktail (as above). The membrane preparation was aliquoted and stored at −80° C. Protein concentration of the membrane preparation was determined in a sample by means of a commercial protein assay (Bio-Rad, DC Protein Assay, cat. nos. 500-0113, 500-0114, 500-0115).

(c) GTP-γ-S-Assay

The Edg-1 membrane preparation obtained in (b) was employed in a commercially available scintillation proximity assay (SPA) kit for G-protein coupled receptor binding from Amersham Biosciences/GE Healthcare (code RPNQ0210), in which ligand-induced binding of $^{35}$S-radiolabeled GTP-γ-S to the receptor-containing membrane, which is bound to scintillation beads, stimulates the emission of light and allows the quantification of the in vitro activity of the Edg-1 agonistic compound. The assay was performed on a 96-well plate substantially according to the manufacturer's instructions. Before starting the experiments, scintillation beads were suspended in a reconstitution buffer consisting of Tris-HCl (pH 7.4) supplemented with 0.1% (w/v) sodium azide and subsequently diluted on ice with assay buffer (consisting of 20 mM HEPES, 100 mM NaCl, 1 mM EDTA (as above), 1 mM dithiothreitol (DTT), adjusted to pH 7.4) to a final bead concentration of 30 mg/ml.

Wells were charged with 10 µl of the specified assay buffer, 10 µl of a 100 µM guanosine diphosphate (GDP) solution, and 10 µl of a solution of the test compound in assay buffer/dimethyl sulfoxide resulting in a final concentration of the test compound of 10 µM. For the high controls, 10 µl of a solution of sphingosine-1-phosphate (S1P; Sigma, cat. no. S-9666), resulting in a final S1P concentration of 10 µM, and for the low controls 10 µl of assay buffer, was added into the respective wells instead of the solution of the test compound. All wells contained equivalent amounts of dimethyl sulfoxide. Then 10 µl of a [$^{35}$S]GTP-γ-S solution (4 nM) and the Edg-1 membrane preparation obtained in (b) (15 µg membrane protein in 100 µl of assay buffer) were added to each well. After incubation of the plates at room temperature for a period of 5 min, 50 µl of the specified scintillation bead suspension (30 mg/ml) was added. After a further incubation period of 45 min at room temperature, plates were centrifuged for 10 min at 500×g. Quantification of [$^{35}$S]GTP-γ-S binding and thus receptor activation was measured by means of a beta counter (MicroBeta, Wallac) over 1 min. Values were background-corrected by subtraction of the respective low control. All measurements were made in triplicate. The receptor activation by the test compound is expressed in percent of the respective high control (10 µM S1P, regarded as 100% activation). In Table 2 activations observed with example compounds at 10 µM are listed.

TABLE 2

Edg-1 receptor activation by example compounds at 10 µM in percent of the activation by 10 µM S1P

| Example | % activation |
|---------|--------------|
| 1 | 94 |
| 2 | 97 |
| 3 | 92 |
| 4 | 106 |
| 5 | 86 |
| 6 | 118 |
| 7 | 38 |
| 8 | 98 |
| 9 | 90 |

It can be seen from the measurement data that the compounds are highly suitable for wound healing and in particular for treating wound healing disorders of patients with diabetes.

The invention claimed is:

1. A compound of formula I, or a physiologically acceptable salt thereof, or a physiologically acceptable solvate of said compound or solvate of the salt,

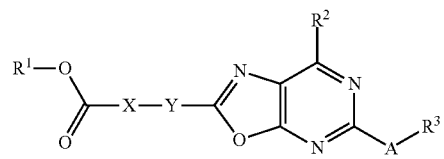

wherein
A is selected from the group consisting of a bond, —CH$_2$—, NH, O and S;
X is selected from the group consisting of (C$_1$-C$_6$)-alkanediyl, (C$_2$-C$_6$)-alkenediyl, (C$_2$-C$_6$)-alkynediyl, (C$_3$-C$_7$)-cycloalkanediyl, (C$_1$-C$_6$)-alkanediyloxy and (C$_3$-C$_7$)-cycloalkanediyloxy, all of which are optionally substituted by one or more identical or different substituents selected from the group consisting of fluorine and hydroxyl, where the oxygen atom of the (C$_1$-C$_6$)-alkanediyloxy and (C$_3$-C$_7$)-cycloalkanediyloxy groups is attached to group Y;
Y is selected from the group consisting of phenylene and a bivalent radical of an aromatic 5-membered or 6-membered monocyclic heterocycle which contains 1, 2 or 3 identical or different ring heteroatoms selected from the group consisting of N, O and S, where one of the ring nitrogen atoms may carry a hydrogen atom or a substituent R$^4$ and where the phenylene and the bivalent radical of an aromatic heterocycle are optionally substituted at one or more ring carbon atoms by identical or different substituents R$^5$;
R$^1$ is selected from the group consisting of hydrogen, (C$_1$-C$_4$)-alkyl and (C$_3$-C$_7$)-cycloalkyl-C$_z$H$_{2z}$—, where z is selected from the group consisting of 0, 1 and 2;
R$^2$ is selected from the group consisting of (C$_3$-C$_6$)-alkyl, (C$_3$-C$_5$)-cycloalkyl-C$_x$H$_{2x}$—, Het$^1$-C$_n$H$_{2n}$—, where x and n are selected from the group consisting of 0, 1 and 2;
R$^3$ is selected from the group consisting of (C$_1$-C$_6$)-alkyl, where the alkyl radical is optionally substituted by one or more fluorine atoms, (C$_2$-C$_6$)-alkenyl, (C$_2$-C$_6$)-alkynyl, (C$_3$-C$_7$)-cycloalkyl-C$_u$H$_{2u}$— or Het$^2$-C$_v$H$_{2v}$—, where u and v are selected from the group consisting of 1 and 2, or R$^3$ is a radical of a saturated or unsaturated 3-membered to 10-membered monocyclic or bicyclic ring which contains 0, 1, 2, 3 or 4 identical or different ring heteroatoms selected from the group consisting of N, O and S, where one or two of the ring nitrogen atoms may carry a hydrogen atom or a $(C_1-C_4)$-alkyl substituent and one or two of the ring sulfur atoms may carry one or two oxo groups and where the radical of a ring is optionally substituted at one or more ring carbon atoms by identical or different substituents $R^{31}$;

$R^4$ is selected from the group consisting of $(C_1-C_4)$-alkyl, $(C_3-C_7)$-cycloalkyl-$C_wH_{2w}$— and oxy, where w is selected from the group consisting of 0, 1 and 2;

$R^5$ is selected from the group consisting of halogen, hydroxyl, $(C_1-C_4)$-alkyl-, $(C_3-C_5)$-cycloalkyl-$C_zH_{2z}$—, $(C_1-C_4)$-alkyloxy, $(C_1-C_4)$-alkyl-S(O)$_m$—, amino, nitro, cyano, hydroxycarbonyl, $(C_1-C_4)$-alkyloxycarbonyl, aminocarbonyl and aminosulfonyl, where z is selected from the group consisting of 0, 1 and 2;

$R^{31}$ is selected from the group consisting of halogen, hydroxyl, $(C_1-C_4)$-alkyl, $(C_1-C_4)$-alkyloxy, $(C_3-C_7)$-cycloalkyl, oxo, $(C_1-C_4)$-alkyl-S(O)$_m$—, amino, $(C_1-C_4)$-alkylamino, di($(C_1-C_4)$-alkyl)amino, $(C_1-C_4)$-alkylcarbonylamino, $(C_1-C_4)$-alkylsulfonylamino, nitro, cyano, $(C_1-C_4)$-alkylcarbonyl, aminosulfonyl, $(C_1-C_4)$-alkylaminosulfonyl and di($(C_1-C_4)$-alkyl)aminosulfonyl;

Het$^1$ is a radical of a saturated 4-membered to 6-membered monocyclic saturated heterocycle which contains 1 or 2 identical or different ring heteroatoms selected from the group consisting of O and S and which is attached via a ring carbon atom, where a ring sulfur atom may carry one or two oxo groups and where the radical of a heterocycle is optionally substituted by one or more identical or different substituents selected from the group consisting of fluorine and $(C_1-C_4)$-alkyl;

Het$^2$ is a radical of a saturated 4-membered to 7-membered monocyclic heterocycle which contains 1 or 2 identical or different ring heteroatoms selected from the group consisting of N, O and S and which is attached via a ring carbon atom, where the radical of a heterocycle is optionally substituted by one or more identical or different substituents selected from the group consisting of fluorine and $(C_1-C_4)$-alkyl; and m is selected from the group consisting of 0, 1 and 2;

wherein said compound is present in any of its stereoisomeric forms.

2. The compound of the formula I, or a physiologically acceptable salt thereof, or a physiologically acceptable solvate of said compound or solvate of the salt as claimed in claim 1, wherein A is selected from the group consisting of a bond, —CH$_2$—, NH, O and S;

X is selected from the group consisting of $(C_1-C_6)$-alkanediyl, $(C_2-C_6)$-alkenediyl, $(C_2-C_6)$-alkynediyl, $(C_3-C_7)$-cycloalkanediyl, $(C_1-C_6)$-alkanediyloxy and $(C_3-C_7)$-cycloalkanediyloxy; all of which are optionally substituted by one or more identical or different substituents selected from the group consisting of fluorine and hydroxyl, where the oxygen atom of the $(C_1-C_6)$-alkanediyloxy and $(C_3-C_7)$-cycloalkanediyloxy groups is attached to group Y;

Y is selected from the group consisting of phenylene and a bivalent radical of an aromatic 5-membered or 6-membered monocyclic heterocycle which contains 1, 2 or 3 identical or different ring heteroatoms selected from the group consisting of N, O and S, where one of the ring nitrogen atoms may carry a hydrogen atom or a substituent $R^4$ and where the phenylene and the bivalent radical of an aromatic heterocycle are optionally substituted at one or more ring carbon atoms by identical or different substituents $R^5$;

$R^1$ is selected from the group consisting of hydrogen, $(C_1-C_4)$-alkyl and $(C_3-C_7)$-cycloalkyl-$C_zH_{2z}$—, where z is selected from the group consisting of 0, 1 and 2;

$R^2$ is selected from the group consisting of $(C_3-C_6)$-alkyl, $(C_3-C_5)$-cycloalkyl-$C_xH_{2x}$— and Het$^1$-$C_nH_{2n}$—, where x and n are selected from the group consisting of 0, 1 and 2;

$R^3$ is selected from the group consisting of $(C_1-C_6)$-alkyl, where the alkyl radical is optionally substituted by one or more fluorine atoms, $(C_2-C_6)$-alkenyl, $(C_2-C_6)$-alkynyl, $(C_3-C_7)$-cycloalkyl-$C_uH_{2u}$— or Het$^2$-$C_vH_{2v}$—, where u and v are selected from the group consisting of 1 and 2, or $R^3$ is a radical of a saturated or unsaturated 3-membered to 10-membered monocyclic or bicyclic ring which contains 0, 1, 2, 3 or 4 identical or different ring heteroatoms selected from the group consisting of N, O and S, where one or two of the ring nitrogen atoms may carry a hydrogen atom or a $(C_1-C_4)$-alkyl substituent and one or two of the ring sulfur atoms may carry one or two oxo groups and where the radical of a ring is optionally substituted at one or more ring carbon atoms by identical or different substituents $R^{31}$;

$R^4$ is selected from the group consisting of $(C_1-C_4)$-alkyl, $(C_3-C_7)$-cycloalkyl-$C_wH_{2w}$— and oxy, where w is selected from the group consisting of 0, 1 and 2;

$R^5$ is selected from the group consisting of halogen, hydroxyl, $(C_1-C_4)$-alkyl-, $(C_3-C_5)$-cycloalkyl-$C_zH_{2z}$—, $(C_1-C_4)$-alkyloxy, $(C_1-C_4)$-alkyl-S(O)$_m$—, amino, nitro, cyano, hydroxycarbonyl, $(C_1-C_4)$-alkyloxycarbonyl, aminocarbonyl and aminosulfonyl, where z is selected from the group consisting of 0, 1 and 2;

$R^{31}$ is selected from the group consisting of halogen, hydroxyl, $(C_1-C_4)$-alkyl, $(C_1-C_4)$-alkyloxy, $(C_3-C_7)$-cycloalkyl, oxo, $(C_1-C_4)$-alkyl-S(O)$_m$—, amino, $(C_1-C_4)$-alkylamino, di($(C_1-C_4)$-alkyl)amino, $(C_1-C_4)$-alkylcarbonylamino, $(C_1-C_4)$-alkylsulfonylamino, nitro, cyano, $(C_1-C_4)$-alkylcarbonyl, aminosulfonyl, $(C_1-C_4)$-alkylaminosulfonyl and di($(C_1-C_4)$-alkyl)aminosulfonyl;

Het$^1$ is a radical of a saturated 4-membered to 6-membered monocyclic saturated heterocycle which contains 1 or 2 oxygen atoms and which is attached via a ring carbon atom, and where the radical of a heterocycle is optionally substituted by one or more identical or different substituents selected from the group consisting of fluorine and $(C_1-C_4)$-alkyl;

Het$^2$ is a radical of a saturated 4-membered to 7-membered monocyclic heterocycle which contains 1 or 2 identical or different ring heteroatoms selected from the group consisting of O and S and which is attached via a ring carbon atom, where the radical of a heterocycle is optionally substituted by one or more identical or different substituents selected from the group consisting of fluorine and $(C_1-C_4)$-alkyl; and m is selected from the group consisting of 0, 1 and 2;

wherein said compound is present in any of its stereoisomeric forms.

3. The compound of the formula I, or a physiologically acceptable salt thereof, or a physiologically acceptable solvate of said compound or solvate of the salt as claimed in claim 1, wherein A is —CH$_2$— or O;

X is $(C_1-C_6)$-alkanediyloxy, where the oxygen atom of the $(C_1-C_6)$-alkanediyloxy group is attached to group Y;

Y is phenylene, where the phenylene is optionally substituted at one or more ring carbon atoms by identical or different substituents $R^5$;

$R^1$ is hydrogen or $(C_1-C_4)$-alkyl;

$R^2$ is $(C_3-C_6)$-alkyl;

$R^3$ is $(C_1-C_6)$-alkyl, where the alkyl radical is optionally substituted by one or more fluorine atoms, or phenyl, where the phenyl radical is optionally substituted at one or more ring carbon atoms by identical or different substituents $R^{31}$;

$R^5$ is halogen, hydroxyl, $(C_1-C_4)$-alkyl-, $(C_3-C_5)$-cycloalkyl-$C_zH_{2z}$—, $(C_1-C_4)$-alkyloxy, $(C_1-C_4)$-alkyl-S(O)$_m$—, amino, nitro, cyano, hydroxycarbonyl, $(C_1-C_4)$-alkyloxycarbonyl, aminocarbonyl or aminosulfonyl, where z is selected from the group consisting of 0, 1 and 2;

$R^{31}$ is halogen, $(C_1-C_4)$-alkyl, $(C_3-C_7)$-cycloalkyl, hydroxyl, $(C_1-C_4)$-alkyloxy, oxo, $(C_1-C_4)$-alkyl-S(O)$_m$—, amino, $(C_1-C_4)$-alkylamino, di$((C_1-C_4)$-alkyl)amino, $(C_1-C_4)$-alkylcarbonylamino, $(C_1-C_4)$-alkylsulfonylamino, nitro, cyano, $(C_1-C_4)$-alkylcarbonyl, aminosulfonyl, $(C_1-C_4)$-alkylaminosulfonyl or di$((C_1-C_4)$-alkyl)aminosulfonyl; and m is selected from the group consisting of 0, 1 and 2;

wherein said compound is present in any of its stereoisomeric forms.

4. The compound of the formula I, or a physiologically acceptable salt thereof, or a physiologically acceptable solvate of said compound or solvate of the salt as claimed in claim 1, wherein A is —CH$_2$— or O;

X is $(C_1-C_6)$-alkanediyloxy, where the oxygen atom of the $(C_1-C_6)$-alkanediyloxy group is attached to group Y;

Y is phenylene, where the phenylene is optionally substituted at one or more ring carbon atoms by identical or different substituents $R^5$;

$R^1$ is hydrogen;

$R^2$ is $(C_3-C_6)$-alkyl;

$R^3$ is $(C_1-C_6)$-alkyl, where the alkyl radical is optionally substituted by one or more fluorine atoms, or phenyl, where the phenyl radical is optionally substituted at one or more ring carbon atoms by identical or different substituents $R^{31}$;

$R^5$ is $(C_1-C_4)$-alkyl; and $R^{31}$ is halogen;

wherein said compound is present in any of its stereoisomeric forms.

5. A pharmaceutical composition, comprising at least one compound of the formula I as claimed in claim 1 or a physiologically acceptable salt thereof, or a physiologically acceptable solvate of said compound or solvate of the salt, and a pharmaceutically acceptable carrier.

6. The pharmaceutical composition as claimed in claim 5, wherein the pharmaceutical composition is a hydrogel preparation.

7. A pharmaceutical composition, comprising at least one compound of the formula I as claimed in claim 1 or a physiologically acceptable salt thereof, or a physiologically acceptable solvate of said compound or salt of the solvate, and a pharmaceutically acceptable carrier, wherein said compound is present as a mixture of stereoisomeric forms in any ratio.

\* \* \* \* \*